(12) United States Patent
Vad et al.

(10) Patent No.: US 10,058,441 B2
(45) Date of Patent: Aug. 28, 2018

(54) DEPLOYMENT HANDLE FOR A PRE-LOADED ILIAC PROSTHESIS DELIVERY DEVICE

(71) Applicant: COOK MEDICAL TECHNOLOGIES LLC, Bloomington, IN (US)

(72) Inventors: Siddharth Vad, Irvine, CA (US); James A. Teague, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 164 days.

(21) Appl. No.: 15/156,959

(22) Filed: May 17, 2016

(65) Prior Publication Data
US 2016/0338864 A1 Nov. 24, 2016

Related U.S. Application Data

(60) Provisional application No. 62/164,184, filed on May 20, 2015.

(51) Int. Cl.
*A61F 2/95* (2013.01)
*A61F 2/966* (2013.01)
*A61F 2/954* (2013.01)

(52) U.S. Cl.
CPC ............ *A61F 2/954* (2013.01); *A61F 2/95* (2013.01); *A61F 2/966* (2013.01);
(Continued)

(58) Field of Classification Search
CPC .. A61F 2/95; A61F 2/954; A61F 2/966; A61F 2002/9665; A61F 2002/9517; A61F 2002/9505; A61F 2002/9511
See application file for complete search history.

(56) References Cited

U.S. PATENT DOCUMENTS

2005/0080476 A1 4/2005 Gunderson et al.
2012/0221091 A1* 8/2012 Hartly .................. A61F 2/95
623/1.11
(Continued)

FOREIGN PATENT DOCUMENTS

EP 2522315 A1 11/2012
WO WO 2011/049808 A1 4/2011

OTHER PUBLICATIONS

Examination Report for corresponding EP Application No. 16275076, dated Aug. 28, 2017, 4 pages.
(Continued)

*Primary Examiner* — Dinah Baria
(74) *Attorney, Agent, or Firm* — Brinks Gilson & Lione

(57) ABSTRACT

A delivery system for delivering an endovascular prosthesis is disclosed. A handle assembly is disposed at the distal end of the delivery system. The handle assembly includes a main handle and a second handle disposed at least partially on the main handle and longitudinally moveable relative to the main handle. A trigger wire release mechanism is disposed in the interior or the main handle. A sheath is operatively connected to the second handle, such that longitudinal movement of the second handle relative to the main handle retracts the sheath in a distal direction. Movement of the trigger wire release mechanism from a first position to a second deployed position is prevented when the sheath is in the first position. Methods for accessing the iliac arteries and deploying an endovascular prosthesis therein using the delivery system and handle assembly are also disclosed.

20 Claims, 28 Drawing Sheets

(52) U.S. Cl.
CPC .......... *A61F 2002/9505* (2013.01); *A61F 2002/9511* (2013.01); *A61F 2002/9517* (2013.01)

(56) References Cited

U.S. PATENT DOCUMENTS

| | | | |
|---|---|---|---|
| 2014/0121749 A1* | 5/2014 | Roeder | A61F 2/954 623/1.11 |
| 2016/0135972 A1 | 5/2016 | Vad et al. | |
| 2016/0184117 A1 | 6/2016 | Vad et al. | |

OTHER PUBLICATIONS

Partial European Search Report for corresponding EP 16275076, dated Oct. 7, 2016, 7 pages.

\* cited by examiner

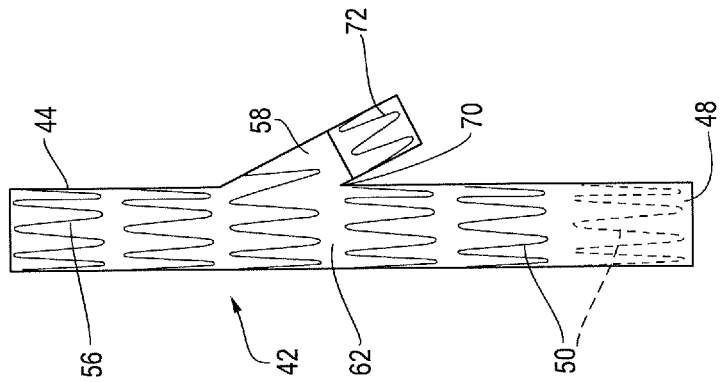
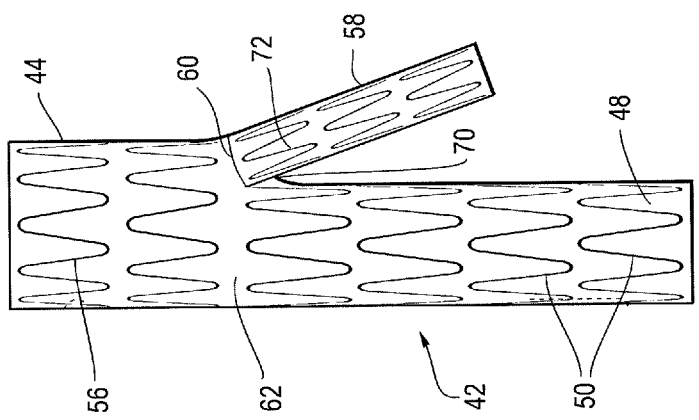

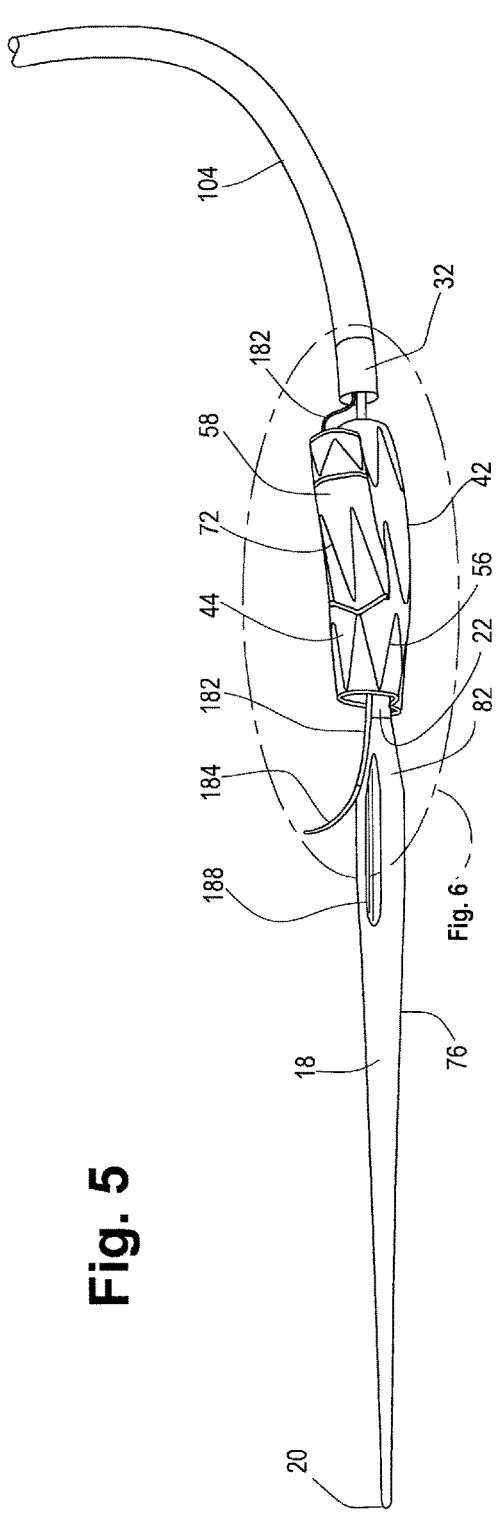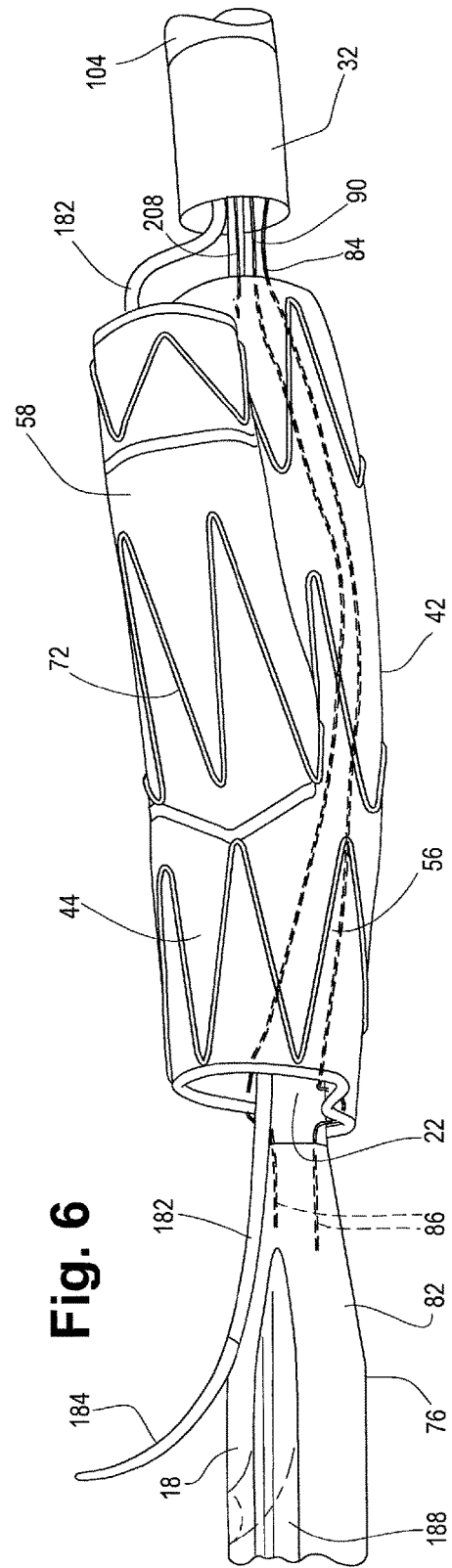

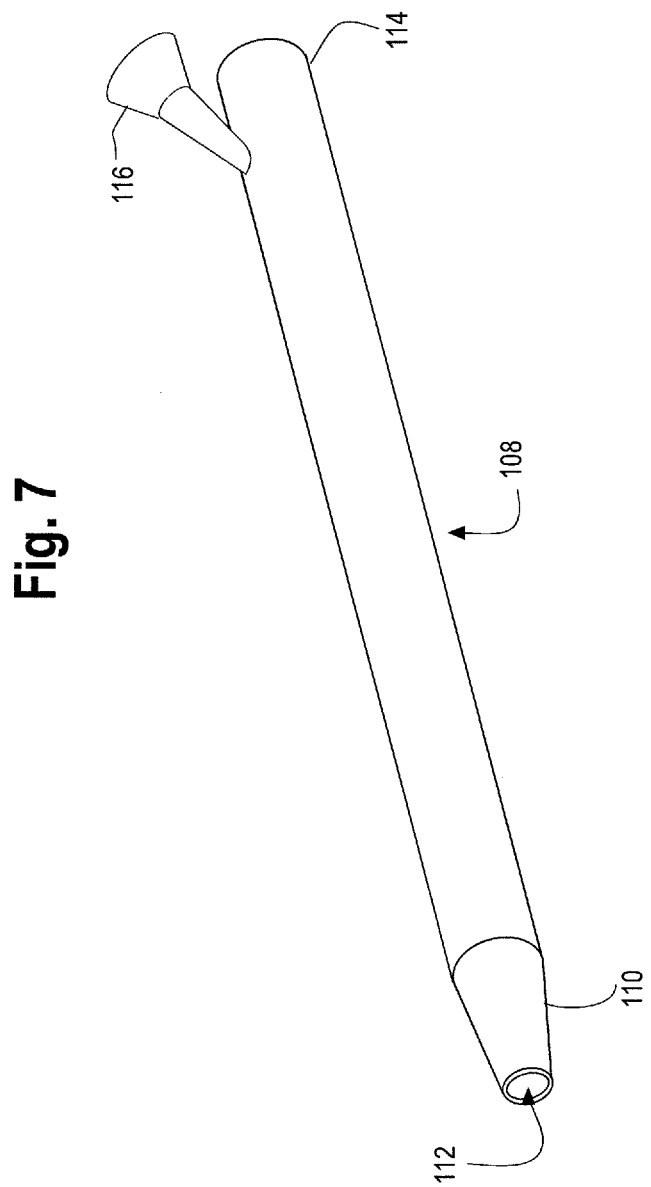

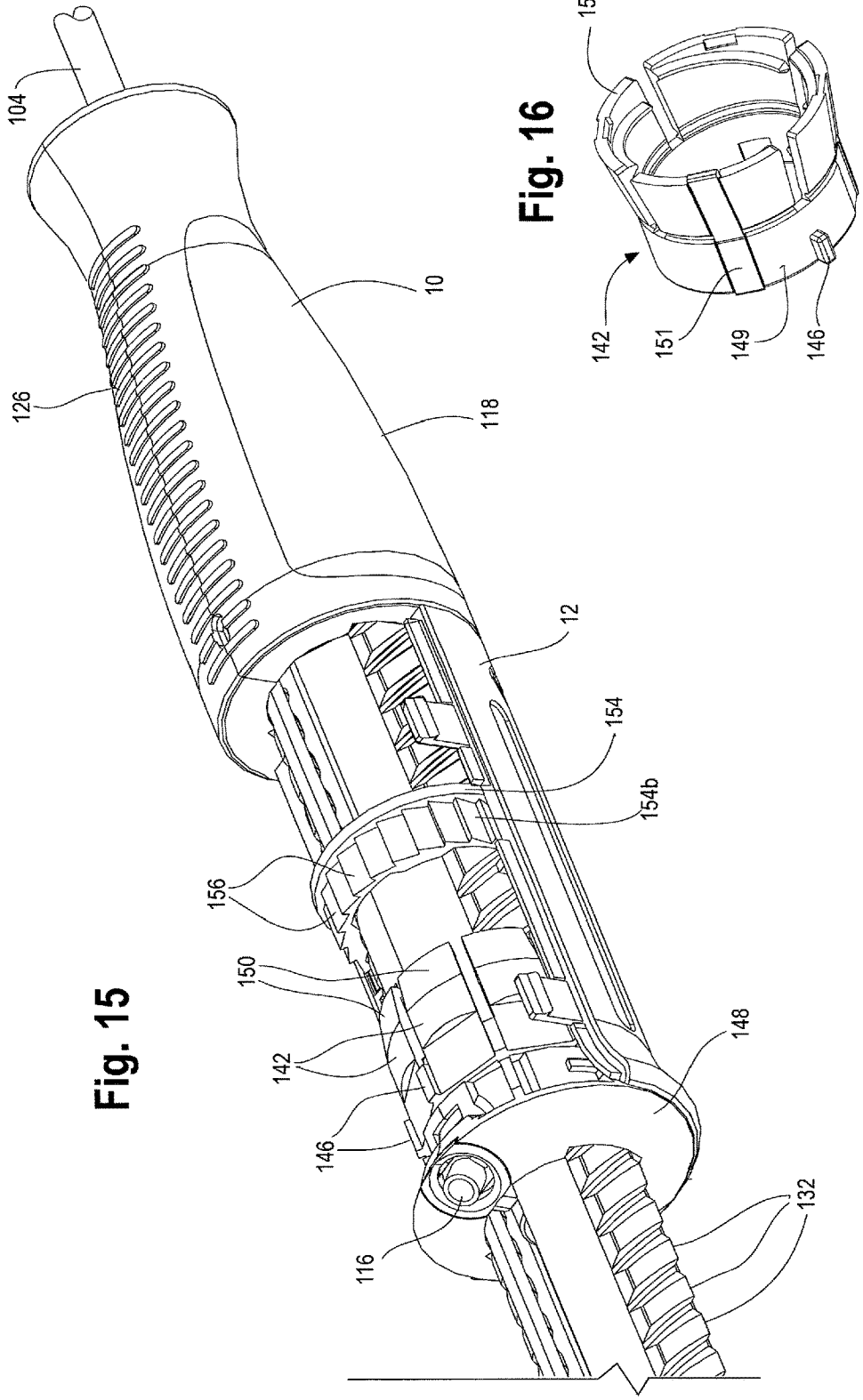
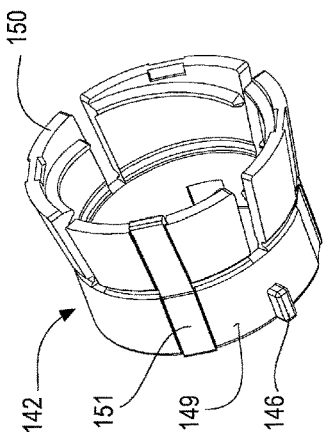
Fig. 15
Fig. 16

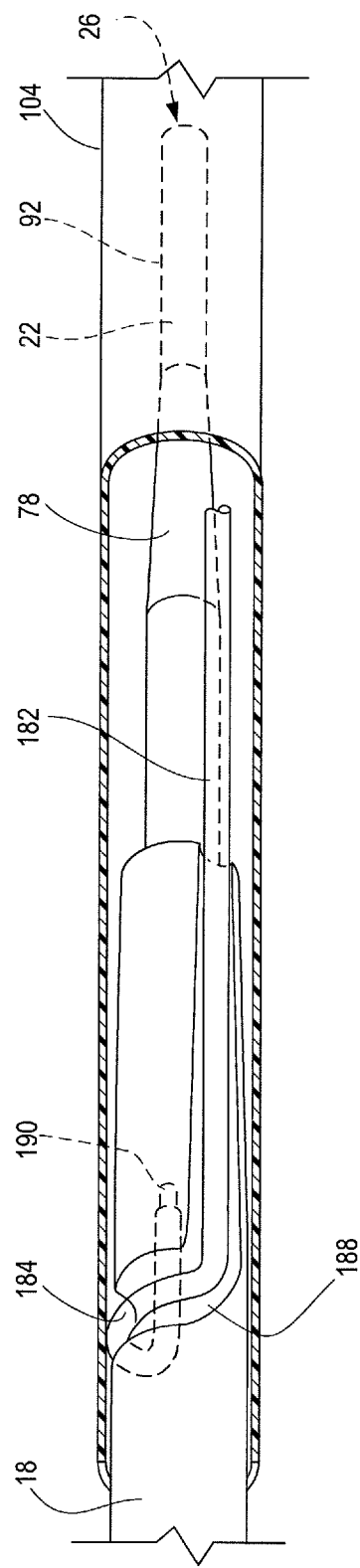
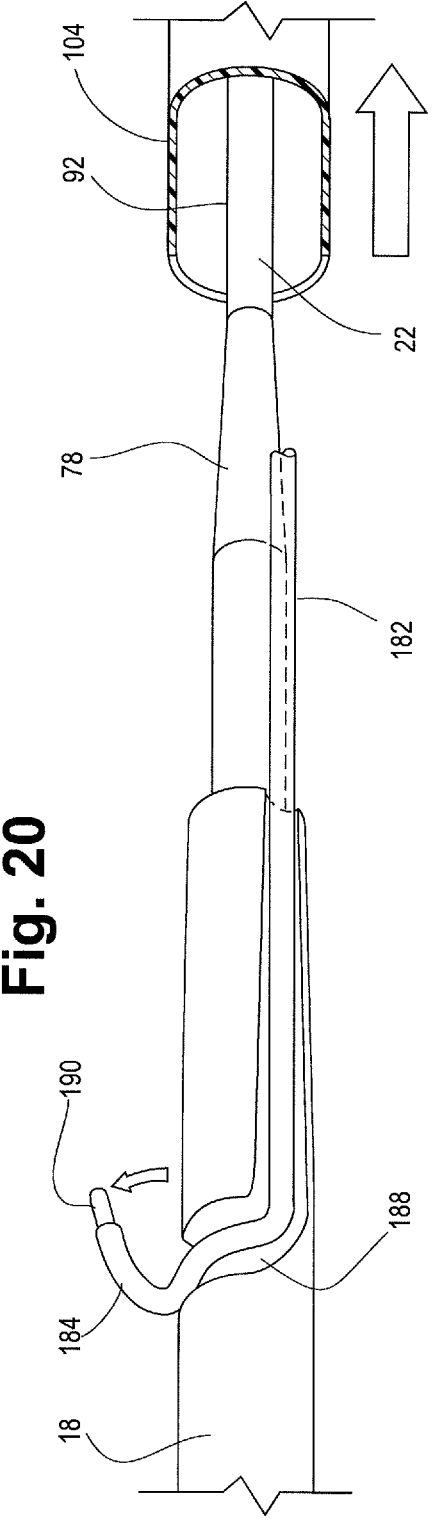
Fig. 19
Fig. 20

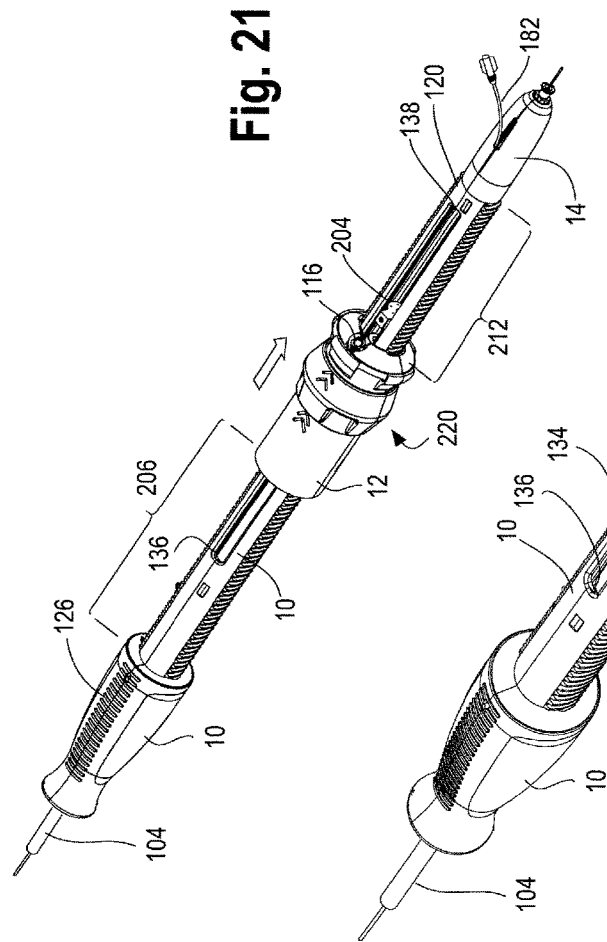

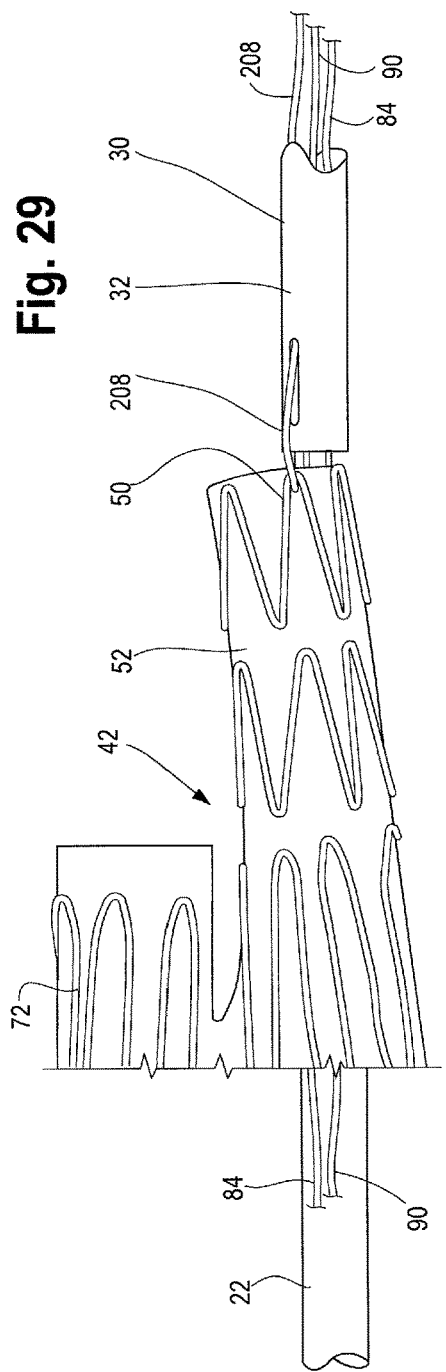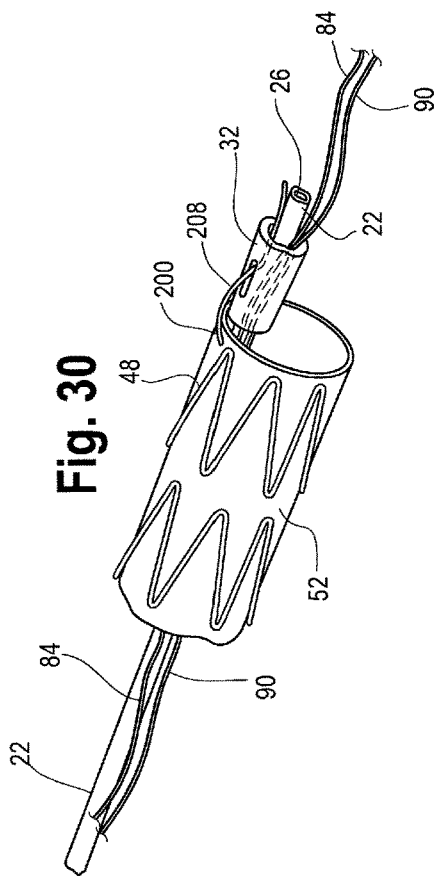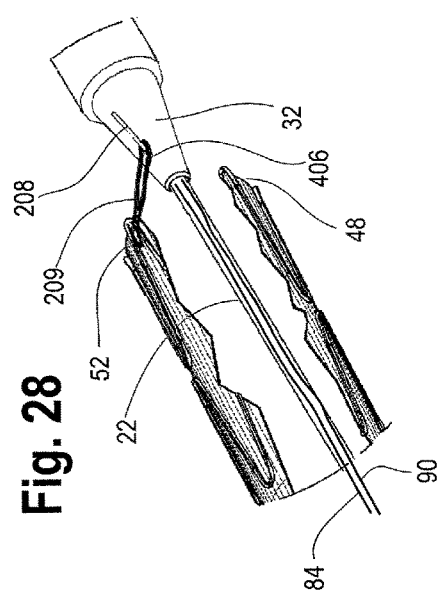

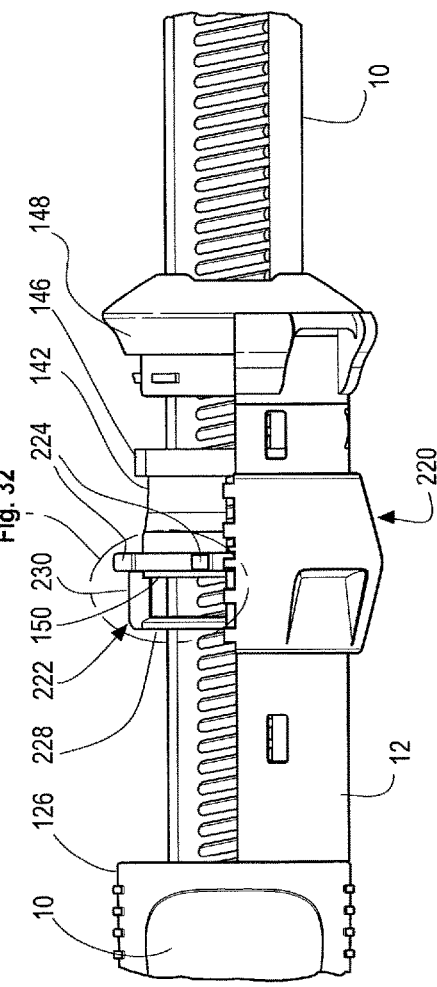
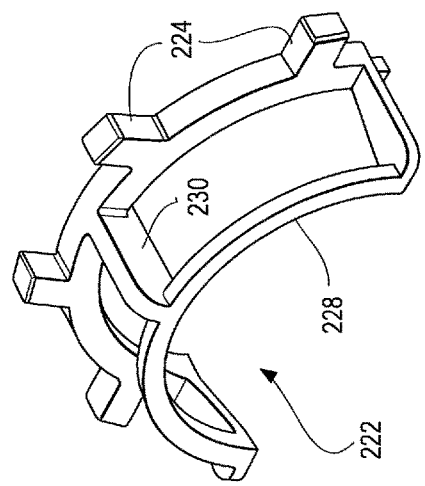
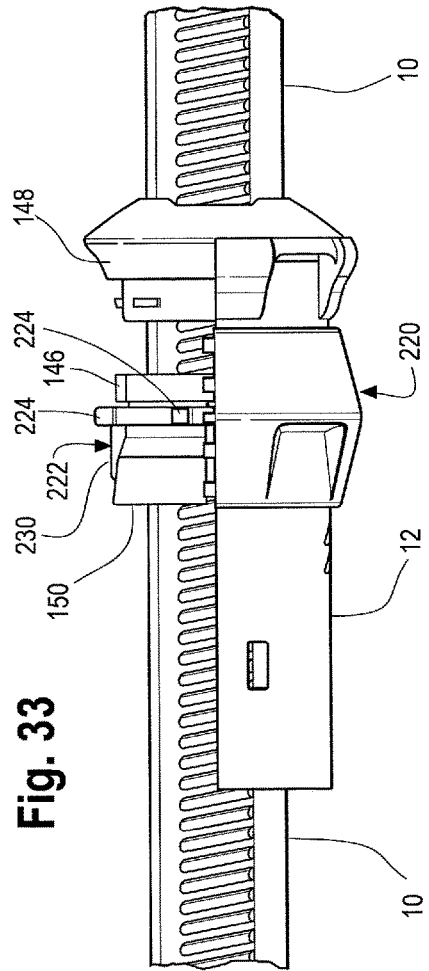

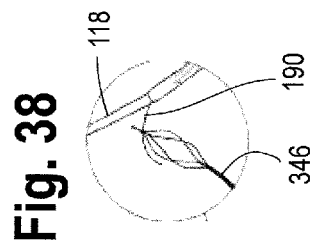
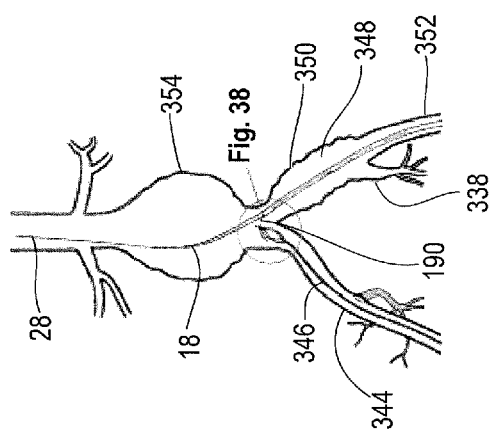
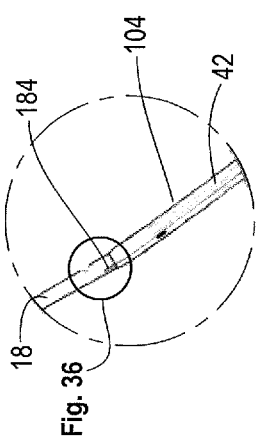
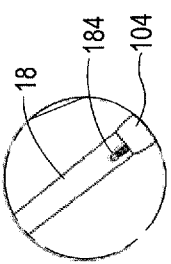
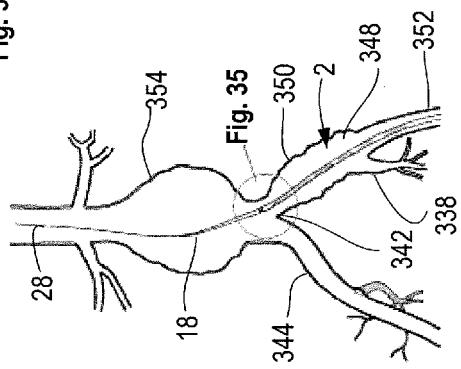

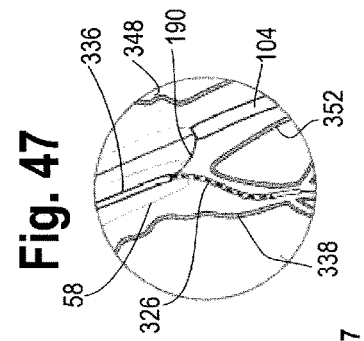
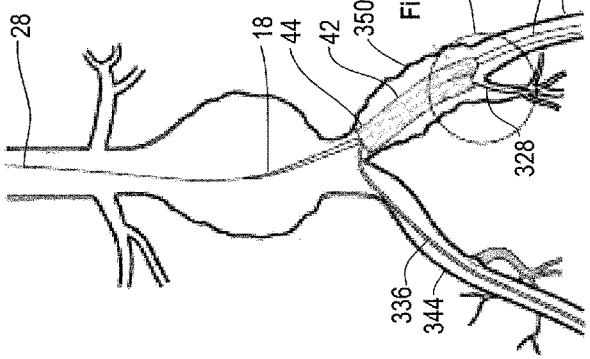
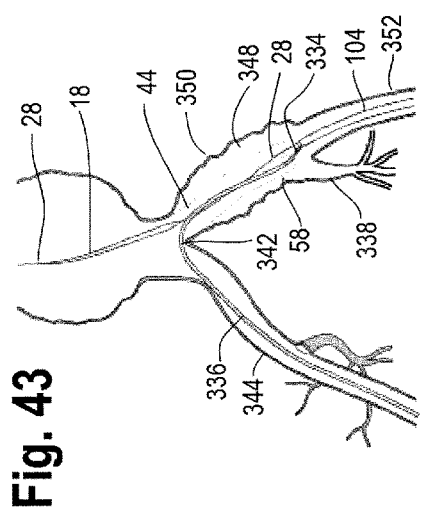
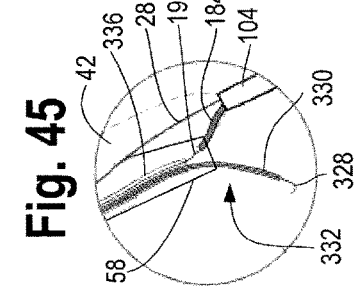
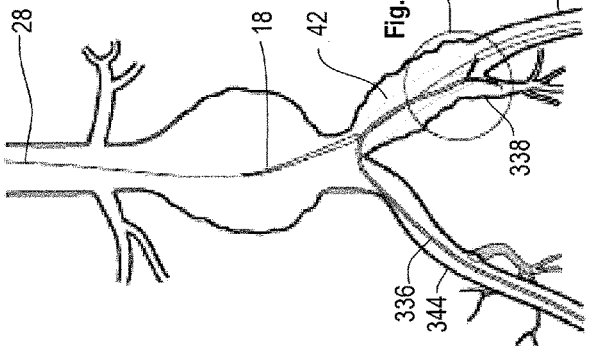

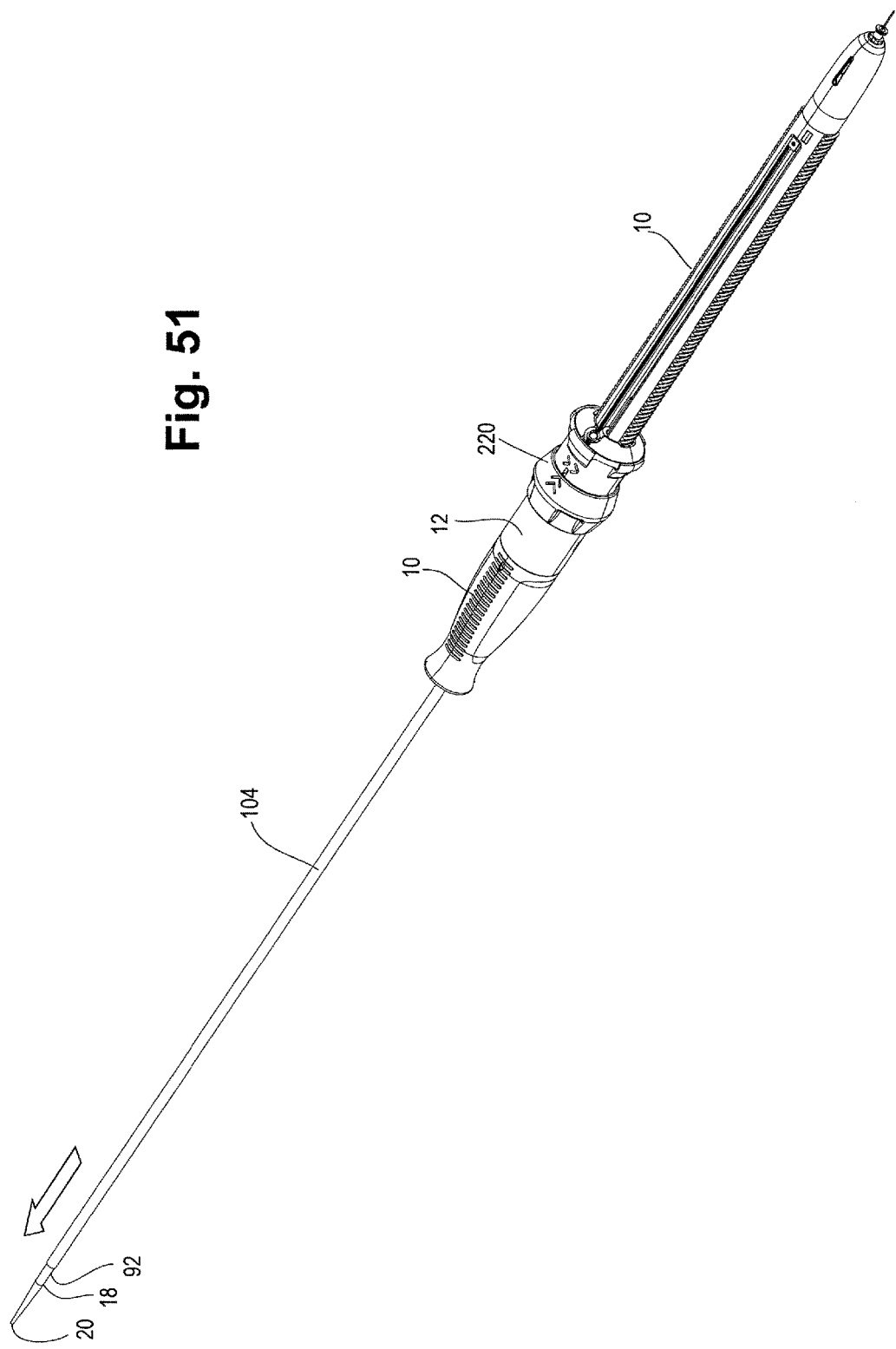

DEPLOYMENT HANDLE FOR A PRE-LOADED ILIAC PROSTHESIS DELIVERY DEVICE

CROSS-REFERENCE TO RELATED APPLICATIONS

This application claims the benefit of U.S. Provisional Application Ser. No. 62/164,184, filed May 20, 2015, which is incorporated by reference herein in its entirety.

BACKGROUND

This invention relates generally to medical devices and methods of using the same, and more particularly, to an endovascular prosthesis delivery device and methods for placement and deployment of the prosthesis in the lumen of a vessel.

Endovascular prostheses, such as a stent, stent-graft, vena cava filter or occlusion device, may be inserted into an anatomical vessel or duct for various purposes. For example, a stent graft may be delivered intraluminally from the femoral artery for treatment of vasculature in the human or animal body to bypass a repair or defect in the vasculature or to maintain or restore patency in a formerly blocked or constricted passageway. The stent graft may extend proximally and/or distally away from a vascular defect, including a diseased portion of an aneurysm, and engage a healthy portion of a vessel wall.

In many cases, the damaged or defective portion of the vasculature may include a branched or side vessel such as a common iliac artery and/or an internal iliac artery and external iliac artery extending from the common iliac artery. Commonly, to repair a defect in these branched vessels, a stent graft is provided which, when deployed in the common iliac artery, has a side arm or fenestration positioned towards the opening to the internal iliac artery. If desired, an extension stent graft can be deployed through the side arm or fenestration into the internal iliac artery to bypass a diseased portion thereof and restore the blood flow path to the internal iliac artery.

The stent graft to be implanted may be coupled to a delivery device in a compressed state and then released from the delivery device so as to expand within the vessel. The delivery device may then be withdrawn, leaving the stent graft in position within the vessel. Oftentimes, the steps to carry out the deployment of the stent graft may occur in a pre-determined deployment sequence. For example, the delivery device may first be positioned within the vessel, then the sheath retracted to allow the stent graft to at least partially expand. Further steps may then be performed, for example, that facilitate release of one or both ends of the stent graft, to deploy an anchoring stent, and the like. In most cases, it is desirable that such deployment steps follow a specific order as instructed by the manufacturer of the device. The delivery device described herein comprises a handle assembly that permits controlled and sequential release and deployment of a stent graft from the delivery device.

While this invention will be generally discussed in relation to a delivery device for a stent graft and method of deployment thereof into a common iliac artery and/or into an internal iliac artery, it is also contemplated that the invention is not so limited and may relate to any body or vessel lumen in which such a deployment is necessary or desired.

SUMMARY

The present disclosure provides a handle assembly and a delivery system for delivering and deploying an endovascular graft into one or more branched vessels.

In one example, a handle assembly for a prosthesis delivery device is disclosed. The handle assembly comprises a main handle comprising a proximal end and a distal end and sidewall extending there between to define a main handle housing interior. A second handle is disposed at least partially on the main handle and is longitudinally moveable relative to the main handle. A trigger wire release mechanism is disposed in the main handle housing interior and wherein at least one proximal trigger wire extends from the trigger wire release mechanism to a proximal end of a prosthesis and wherein at least one distal trigger wire extends from the trigger wire release mechanism to a distal end of the prosthesis. Longitudinal movement of the second handle relative to the main handle causes retraction of the trigger wire release mechanism within the main handle housing interior, thereby releasing the at least one proximal trigger wire from the proximal end of the prosthesis and releasing the at least one distal trigger wire from the distal end of the prosthesis.

In another example, a delivery system for delivering a prosthesis is disclosed. The delivery system comprises a proximal end and a distal end. A prosthesis retention region is located at the proximal end of the delivery system. A prosthesis is releasably coupled to the prosthesis retention region of the delivery system. The prosthesis comprises a proximal end and a distal end and a sidewall extending there between, and a side arm extending from the sidewall of the prosthesis between the proximal and distal ends. A handle assembly is disposed at the distal end of the delivery device. In one example, the handle assembly comprises a main handle comprising a proximal end and a distal end and sidewall extending there between to define a main handle housing interior. A second handle is disposed at least partially on the main handle and longitudinally moveable relative to the main handle. A trigger wire release mechanism is disposed in the main handle housing interior, the trigger wire release mechanism having a first position within the main handle housing in which the prosthesis is retained in a delivery configuration and a second position in which the prosthesis is in a deployed configuration. A sheath is operatively connected to the second handle and extends proximally of the main handle, the sheath having a first position wherein the prosthesis is covered by the sheath and a second position, and wherein longitudinal movement of the second handle relative to the main handle retracts the sheath in a distal direction from the first position to the second position. Movement of the trigger wire release mechanism from the first position to the second deployed position is prevented when the sheath is in the first position.

BRIEF DESCRIPTION OF THE DRAWINGS

FIG. 3 is an exemplary stent graft that may be delivered and deployed within the vasculature of a patient.

FIG. 4 is another exemplary stent graft that may be delivered and deployed within the vasculature of a patient.

FIG. 5 illustrates one example of a stent graft releasably coupled to the proximal end of the delivery device and a catheter extending through the stent graft.

FIG. 6 is an enlarged view of a portion of FIG. 5.

FIG. 7 is a front perspective view of a sheath connector component of the handle assembly.

FIG. 15 is an enlarged perspective view of the handle assembly with a portion of the second handle removed.

FIG. 16 is a perspective view of one example of a nut mechanism of the handle assembly.

FIG. 19 is a partial cross-sectional side view of the sheath extending proximally to cover the catheter and at least a distal end of the nose cone.

FIG. 20 illustrates the sheath retracted from the distal end of the nose cone to expose a proximal end of the catheter.

FIG. 21 is a perspective view of the handle assembly after the sheath has been at least partially retracted by moving the second handle distally relative to the main handle.

FIG. 22 is a perspective view of the handle assembly of FIG. 21 with a portion of the second handle and outer ring removed to illustrate the sleeve in a distal position and the nut disengaged from the main handle.

FIG. 28 illustrates one example of a trigger wire releasably coupled to the distal end of a stent graft.

FIG. 29 illustrates another example of a trigger wire releasably coupled to the distal end of a stent graft.

FIG. 30 illustrates yet another example of a trigger wire releasably coupled to the distal end of a stent graft.

FIG. 31 is a side view of one example of a nut and a sleeve in a proximal position retaining the nut into engagement with the main handle.

FIG. 32 is a perspective view of one example of a sleeve.

FIG. 33 is a side view of one example of a nut with the sleeve moved distally causing the nut to flare radially outwardly and disengage from the main handle.

FIG. 34 illustrates the delivery device of FIG. 1 being tracked to a desired location within a patient's vasculature during delivery and deployment of a stent graft.

FIG. 35 is an enlarged view of a portion of the device of FIG. 34 illustrating a sheath extending to the nose cone and a pre-loaded catheter and guide wire extending proximally through the sheath and beyond the proximal end of a sheath.

FIG. 36 is an enlarged view of FIG. 35 illustrating the proximal tip of the pre-loaded catheter and guide wire extending beyond the proximal end of the sheath.

FIG. 37 illustrates the delivery device in the vasculature and the guide wire being snared from the contralateral iliac artery.

FIG. 38 is an enlarged view of FIG. 37 showing the guide wire being snared from the contralateral side to create a "through and through" wire.

FIG. 43 illustrates the up and over sheath of FIG. 42 being tracked over the aortic bifurcation and then distally into the proximal end of the stent graft.

FIG. 44 illustrates a secondary delivery assembly being tracked through the up and over sheath and into the side arm of the stent graft towards to opening of the internal iliac artery.

FIG. 45 illustrates an enlarged portion of FIG. 44.

FIG. 46 illustrates a secondary stent graft being introduced into the internal iliac artery.

FIG. 47 illustrates an enlarged portion of FIG. 46.

FIG. 51 is a perspective view of the delivery device with the second handle moved proximally with the proximal tip re-sheathed and configured for withdrawal of the device from a patient.

DETAILED DESCRIPTION

Figure 1:
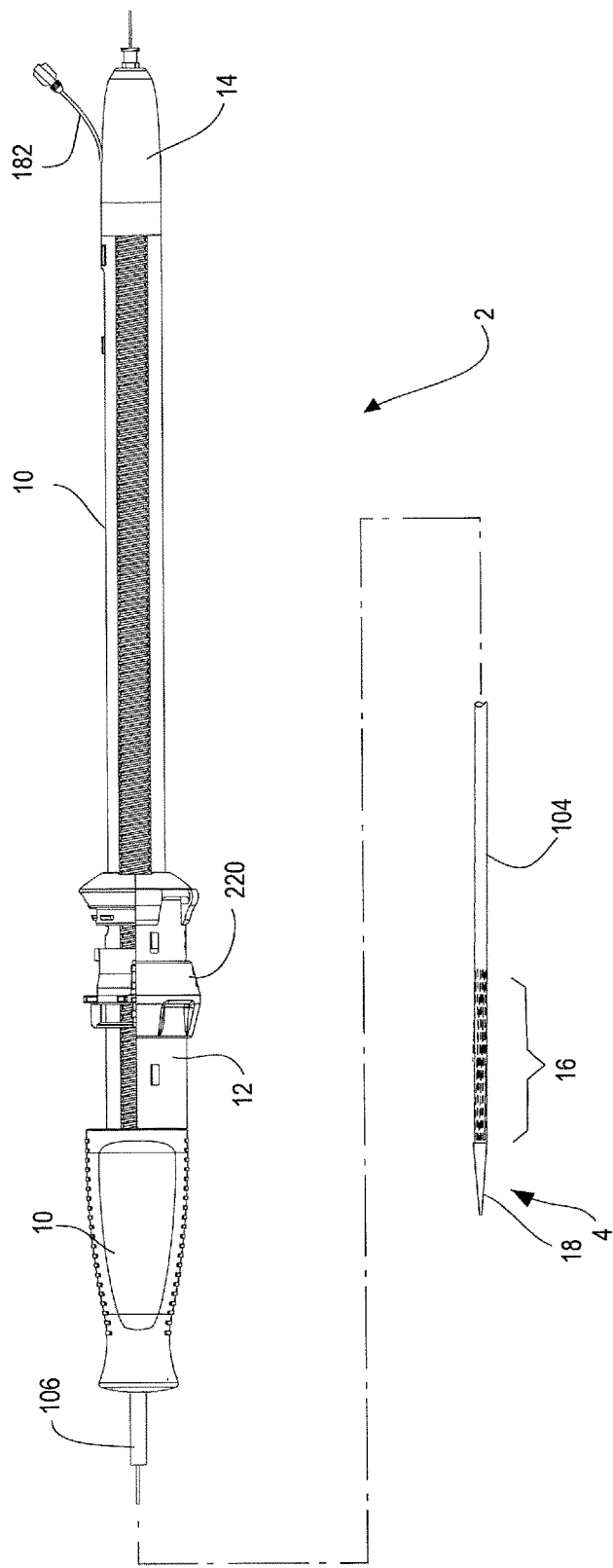
FIG. 1 is a side view of a prosthesis delivery device with an example of a handle assembly at the distal end and a prosthesis retained beneath a sheath at the proximal end.

In this description, when referring to a prosthesis delivery device, proximal refers to the part of the delivery device that is furthest from the operator and intended for insertion in a patient's body and distal refers to that part of the delivery device closest to the operator. With regard to the prosthesis, the term proximal refers to that part of the prosthesis that is closest to the proximal end of the delivery device and distal refers to the opposite end of the prosthesis. The term "ipsilateral" is used to indicate that the diseased vessel(s) being accessed during a given procedure are on the same side of the body (right or left) as the vascular access delivery device/introducer, while "contralateral" signifies that the vessel(s) of interest are on the opposite side of the body.

In general and described in more detail below with reference to the reference numbers and Figures, the delivery device 2 includes a proximal end 4 and a distal end 6. A handle assembly 8 is located adjacent the distal end of the device. One example of a handle assembly 8 is described in detail below and also described in U.S. Provisional patent application 62/074,766 filed Nov. 4, 2014, entitled "Deployment Handle For A Prosthesis Delivery Device", and U.S. Provisional patent application 62/097,244 filed Dec. 29, 2014, entitled Deployment Handle For A Delivery Device With Mechanism For Quick Release Of A Prosthesis And Re-Sheathing Of Device Tip," which applications are incorporated by reference herein in their entireties. Handle assembly 8 generally includes first or main handle 10 and a second or outer handle 12 and an end cap 14. The main handle 10 is fixed relative to the delivery device 2 and the second handle 12 is disposed on the main handle 10 and is movable longitudinally and/or circumferentially relative to the main handle.

A mechanism within the handle assembly 8 permits the user to implement a "quick release" deployment procedure in which at least a distal portion of a prosthesis can be easily and quickly released from the delivery device 2 and deployed within the patient's vasculature if necessary and/or desired. When deployment of the prosthesis is complete, this same quick release mechanism within the handle assembly 8 may also facilitate re-sheathing or "hubbing" of the proximal end of the delivery device 2, to facilitate removal of the delivery device from the patient's tortious vasculature.

Figure 2:
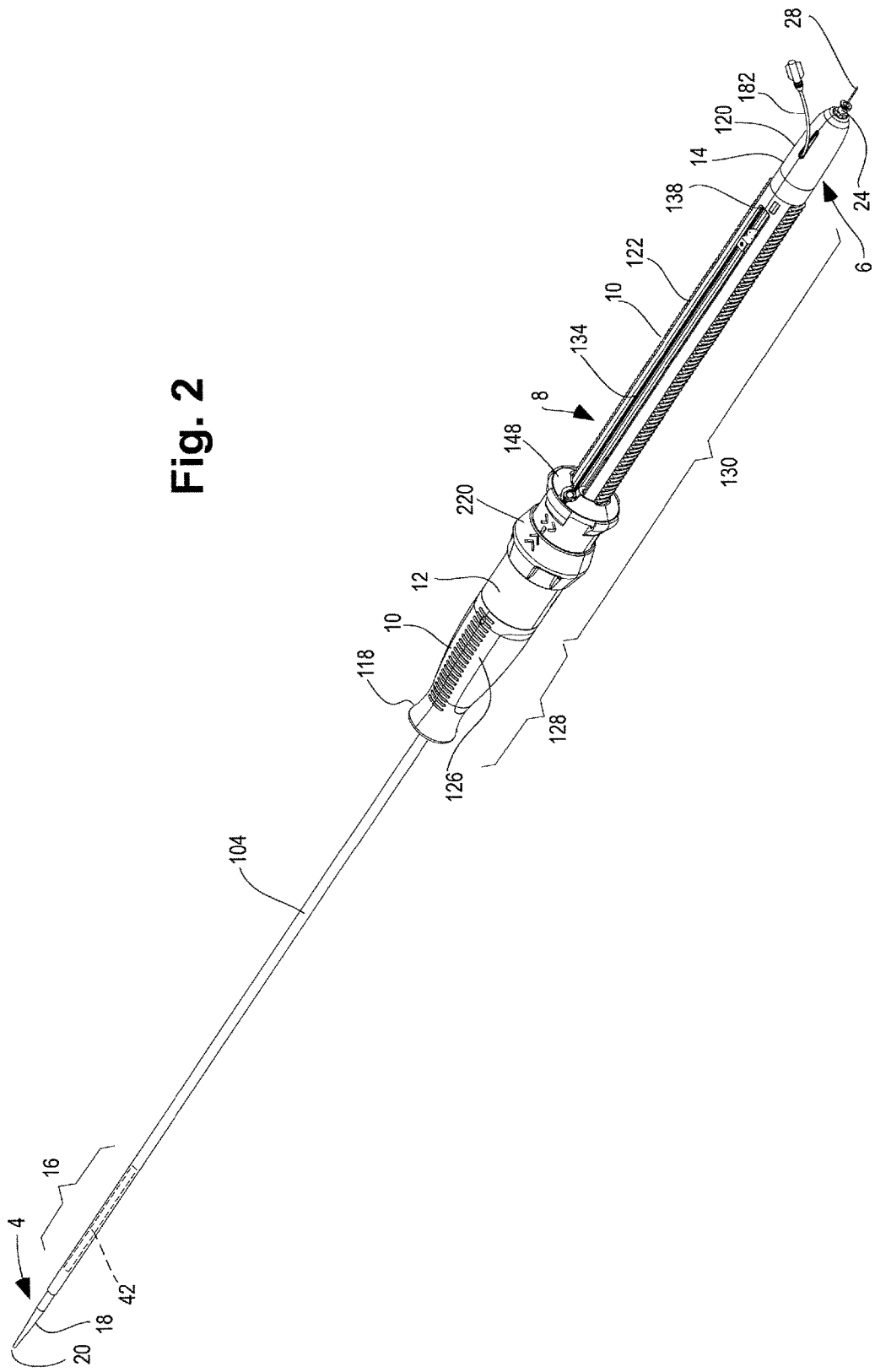
FIG. 2 is a rear perspective view of the delivery device of FIG. 1.

As shown in FIGS. 1 and 2, the proximal end 4 of the delivery device 2 includes stent graft retention region 16 and a tapered nose cone dilator 18 having a proximal tip 20. An inner cannula 22 extends the longitudinal length of the delivery device 2, from a distal flush hub 24 at the distal end 6 of the device 2 to the tapered nose cone dilator 18 at the proximal end 4 of the device 2. Inner cannula 22 has an inner lumen 26 which may accommodate a guide wire 28 for tracking the delivery device 2 to a desired position within a patient's vasculature and which may be used for flushing or injection of fluids. The inner cannula 22 may be made of a variety of suitable materials including a flexible material, polymer, metal and/or alloy, for example, nitinol or stainless steel, and may be either straight or have a curve imparted to a portion of it.

A stiffening cannula, sometimes referred to as a pusher or positioner 30 may be disposed over at least a portion of the inner cannula 22. The positioner 30 may be constructed from various materials, and in one example, a proximal portion 32 of the positioner which is introduced into the patient may comprise a polymer, sometimes referred to as VRDT (or vinyl radiopaque dilator tubing), plastics, metals, alloys or a combination thereof, whereas a distal portion 34 of the positioner 30 may comprise the same material as the proximal portion 32 of the positioner 30 or it may be a different material including but not limited to plastics, polymers, alloys, metals or a combination thereof, that provide sufficient maneuverability and stiffness to the positioner 30 as necessary and desired. The positioner 30 may extend from a location just distal of the stent-graft retention region 16 coaxial with a length of the inner cannula 22, through the main handle 10, and terminate at a distal end 34 within a stationary collar 36 within the main handle 10. The positioner 30 may be retained within the stationary collar 36 by various means, including threaded attachment, adhesives, welding, and/or other suitable attachment mechanism. For a length of the positioner 30, a stiffening rod (not shown) may be disposed over the inner cannula 22 and/or over the positioner 30 for additional stability and maneuverability.

Referring now to FIGS. 3 and 4, at least two exemplary stent grafts 42 are shown, which may be deployed in a controlled and sequential manner using the delivery device 2 described herein. The stent graft 42 is carried on the inner cannula 22 at the stent-graft retention region 16 as shown in FIGS. 1 and 2. The stent-graft 42 has a proximal end 44, a distal end 48, and a series of stents 50 extending the length of the stent graft 42 and attached to the graft material 52.

The proximal end 44 of the stent graft may include a sealing stent 56. Sealing stent 56 may be internal or external to the graft material 52. A series of body stents 50 also are attached to the graft material 52 and may be sutured to the graft material or held to the graft material in other known ways. The series of body stents 50 may be internal or external to the graft material 52, or both. As shown in FIG. 3, all of the stents are external to the graft material 52, while in FIG. 4, the distal-most stent 50 is internal to the graft material 52.

As shown in FIG. 3 and FIG. 4, the stent graft 42 may comprise a side arm or limb 58 extending from the tubular main body 62. The side arm 58 may be integrally formed with the main tubular body 62 and extend from the tubular main body 62 at bifurcation 70. Alternatively, the side arm 58 may be separately formed and attached to the main tubular body, and in one example, the side arm 58 may extend from a fenestration 60 formed in the wall of the main tubular body 62 as shown in FIG. 3. The side arm 58 may also include one or more stents 72 along its length, either internal or external or both. Although FIGS. 3 and 4 show a stent graft 42 having a single side arm 58 extending therefrom, the stent graft may also be a single non-bifurcated tube and/or the stent graft may have one or more fenestrations formed in the graft material 52 and/or one or more additional side branches or arms extending therefrom. Radiopaque markers (not shown) may be placed on various parts of the stent graft 42 to aid in tracking and locating the device at a desired location during a procedure and one or more barbs (not shown) may extend from any one of the body stents 50 or the sealing stent 56 to help anchor the stent graft to the vessel wall.

An exemplary coupling of the stent graft 42 to the delivery device is shown in FIGS. 5 and 6. More specifically, FIGS. 5 and 6 illustrate a proximal end portion 4 of the delivery device 2, and one non-limiting example of an attachment and release mechanism for the proximal end 44 of a stent graft 42 that can be operated using the handle assembly 8 described herein. FIGS. 5 and 6 show the tapered nose cone dilator 18 having a proximal tip 20 and a reverse distal taper 78 at its distal end 82. The surface of the nose cone dilator 18 presents a smooth tapered surface 76 to facilitate entry into and movement through a body vessel. Nose cone dilator 18 may include radiopaque material or be equipped with a radiopaque marker (not shown) to facilitate visualization of the nose cone dilator 18 in use.

As shown in FIG. 6, an exemplary prosthesis attachment and retention mechanism releasably couples the stent graft to the inner cannula 22. In a non-limiting example, as shown in enlarged view in FIG. 6, the attachment and release mechanism comprises at least one trigger wire 84 having a proximal end 86 and a distal end 88. However, other attachment and release mechanisms, including an additional trigger wire 90 also having a proximal end 86 may also be used to releasably couple the proximal end 44 of the stent graft 42 to the inner cannula 22. Other attachment and release mechanisms, in addition to the one or more trigger wires 84, 90 may also be used to couple the proximal end 44 of the stent graft 42 to the delivery device 2, such as diameter reducing ties, a retractable sheath, sutures and the like as will be recognized by one of skill in the art.

In one non-limiting example, the proximal trigger wires 84 and 90 may extend from the handle assembly 8, within positioner 30, and along the outer surface 92 of the inner cannula 22 to the proximal end 44 of the stent graft. More particularly, the distal ends 88 of the proximal trigger wires 84, 90 may be coupled to a trigger wire release mechanism or knob 204 located within the main handle interior 124, such as by adhesives, welding, crimping or by set screws 214 (as will be described in further detail below in connection with FIG. 25). From the trigger wire knob 204, the proximal trigger wires 84, 90 extend proximally along the outer surface of the positioner 30 for a distance, then enter the lumen of the positioner 30 and extend proximally to the proximal end 44 of the stent graft 42. The proximal ends 86 of the trigger wires 84, 90 are releasably coupled to the proximal end 44 of the stent graft 42 as shown in FIG. 6.

In one example, the proximal trigger wires 84, 90 may be directly or indirectly attached to the proximal end 44 of the stent graft 42. For example, the proximal trigger wires 84, 90 may engage a suture loop (not shown) which is attached to the proximal end 44 of the stent-graft 42. In this way, the trigger wires may not weave directly through the graft material 52. Alternatively, the proximal trigger wires 84, 90 may be woven directly through or removably attached to the graft material 52 or woven over or through one or more stents 50 and/or 56 at the proximal end of the graft 42. As FIG. 6 shows, the proximal trigger wires 84, 90 are woven directly through the graft material 52 at the proximal end 44 of the stent graft 42 at two spaced apart points around the periphery of the tubular graft body 62 such that when those points are retained by the trigger wires against the inner cannula 22, the stent graft 42 generally forms a "FIG. 8" formation with one lobe of the "FIG. 8" being slightly larger than the other lobe of the "FIG. 8." Of course, other points of attachment may also be used to releasably couple the stent graft 42 to the inner cannula 22 to form various configurations at the proximal end 44 of the stent graft 42. As FIG. 6 shows, the proximal ends 86 of the trigger wires 84, 90 may be retained within the distal end of the nose cone, such as by friction fit or other suitable attachment means that allow for the trigger wires to be pulled distally and released from the inner cannula when deployment of the proximal end of the stent graft 42 is necessary or desired. Other suitable attachment methods or mechanisms may be used to removably attach the proximal trigger wires 84, 90 to the proximal end of the stent graft 42 as would be recognized by one of skill in the art.

Upon retraction of the trigger wires 84, 90, the proximal end 44 of the stent graft 42 can at least partially deploy radially outwardly within the vessel. If other diameter reducing ties are being used to radially restrain the proximal end 44 of the stent graft 42, those ties must also be removed to allow the proximal end 44 of the stent graft to fully deploy from the inner cannula 22 within the vessel.

As shown in FIGS. 1, 5 and 6, a prosthesis, such as stent graft 42, is disposed on the inner cannula 22 at the proximal end 4 of the delivery device 2 at stent graft retention region 16. The stent graft 42 has an uncoupled state in which the graft is positioned coaxially over the inner cannula 22 with the proximal end 44 of the stent graft 42 in longitudinal proximity relative to the distal end 82 of the nose cone dilator 18. During assembly, the proximal ends 86 of the trigger wires 84, 90 can be woven directly through the graft material 52 at one or more points at the proximal end 44 of the stent graft 42, or alternatively, the proximal ends 86 of the trigger wires 84, 90 may be coupled to one of the stents 50 and/or 56 at the proximal end 44 of the stent graft 42. In another example, the proximal ends 86 of the trigger wires 84, 90 can be woven through or around one or more suture loops (not shown) that are secured to the graft material 52 at or near the proximal end 44 of the stent graft to avoid weaving the trigger wires 84, 90 directly through the graft material 52. After weaving through the stent graft 42 (or through one or more of the proximal stents 56, 50 or through one or more suture loops), the proximal ends 86 of the trigger wires 84, 90 may extend proximally into the nose cone, or alternatively, extend back into the inner cannula 22 through one or more apertures (not shown) formed in the inner cannula. The proximal ends 86 of the trigger wires 84, 90 may be releasably held in place, either within the nose cone or within the inner cannula lumen by friction fit or other releasable attachment mechanisms. When deployment of the stent graft is desired, retraction of the trigger wires 84, 90 allows the proximal end 44 of the stent graft 42 to move from a radially inwardly constrained delivery configuration to a radially outwardly expanded configuration within a vessel, as described further below.

The coupling shown in FIG. 6 releasably secures the stent graft 42 to the inner cannula 22 to radially inwardly restrain the stent graft 42 in a manner that may subsequently facilitate insertion of the subassembly comprising the inner cannula 22 and the stent graft 42 into an outer sheath 104, such as sheath 104 described below. As will be apparent, the outer sheath 104 is configured to radially restrain other regions of the stent graft 42 for delivery in a low-profile configuration to a target site within a patient's anatomy.

As shown in FIG. 1, the longitudinally slideable and retractable sheath 104 extends along the length of the delivery device 2 from the main handle 10 to the nose cone dilator 18. The sheath 104 is configured to cover and assist in retaining a prosthesis, such as stent graft 42, in a radially inwardly compressed, low-profile configuration during delivery of the prosthesis to a target site within a patient's anatomy. The distal end 106 of the sheath 104 is connected within the main handle 10 by a sheath connector 108, which is shown in FIG. 7. In one example, the distal end 106 of the sheath 104 may be slightly flared to facilitate attachment of the sheath 104 to a correspondingly shaped tapered proximal end 110 of the sheath connector 108 as shown in FIG. 7. The distal end 106 of the sheath 104 may be secured to the proximal end 110 of the sheath connector 108 by a friction fit, threaded engagement, adhesives or other attachment mechanisms or combination thereof. The sheath connector 108 has at least one lumen 112 extending from its proximal end 110 to its distal end 114, which allows for sheath connector 108 to travel or slide longitudinally along the positioner 30. The sheath connector 108 also includes a sheath flush port 116, comprising a one way valve that communicates with the sheath connector lumen 112 to allow sheath flushing prior to introduction into the vasculature. An O-ring or silicone disc at the distal end of the sheath connector lumen 112 and a seal within the sheath flush port 116 prevents unintended back flow or leakage of fluid through the sheath connector 108 and flush port 116.

Figure 8:
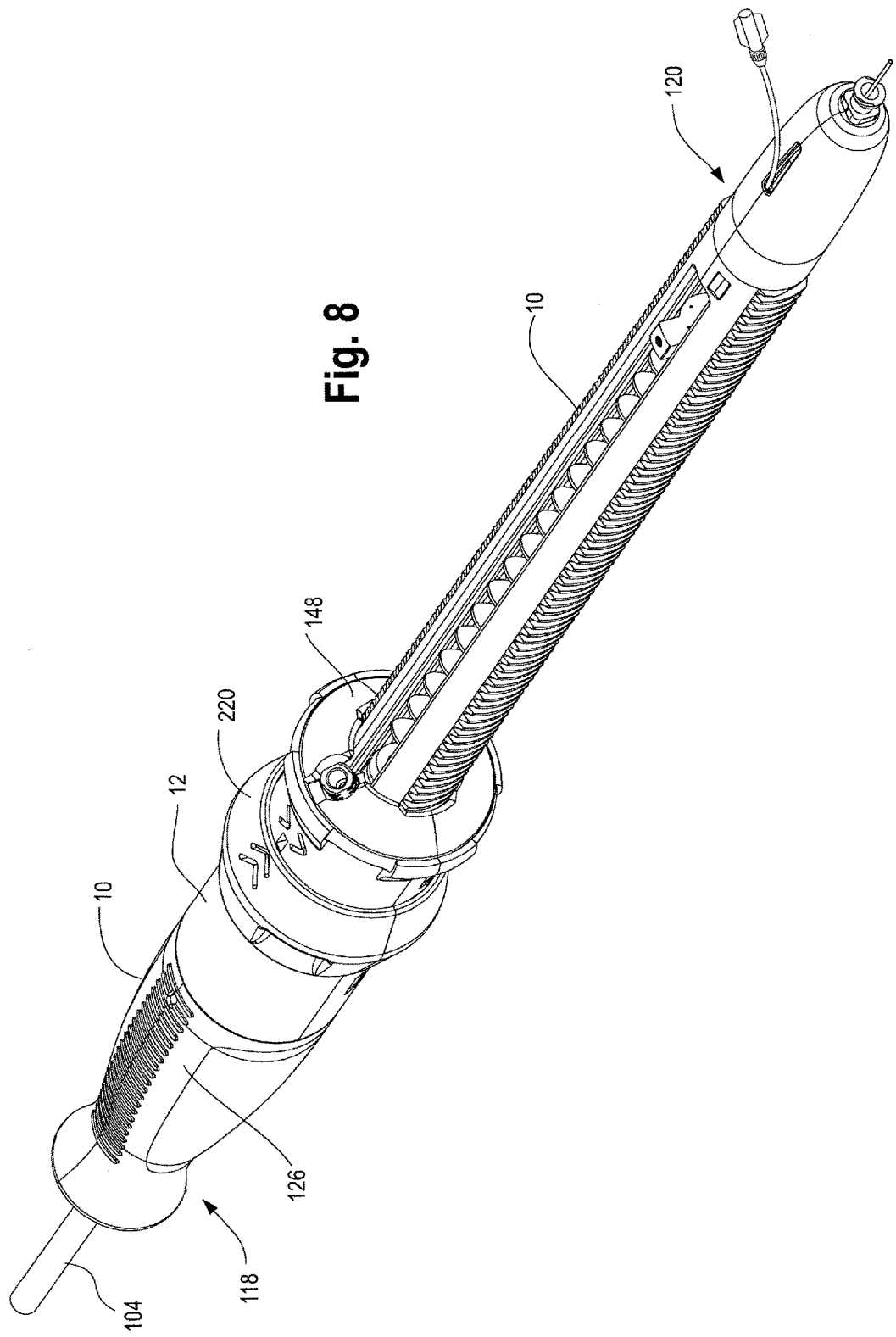
FIG. 8 is a rear perspective view of the handle assembly.
Figure 9:
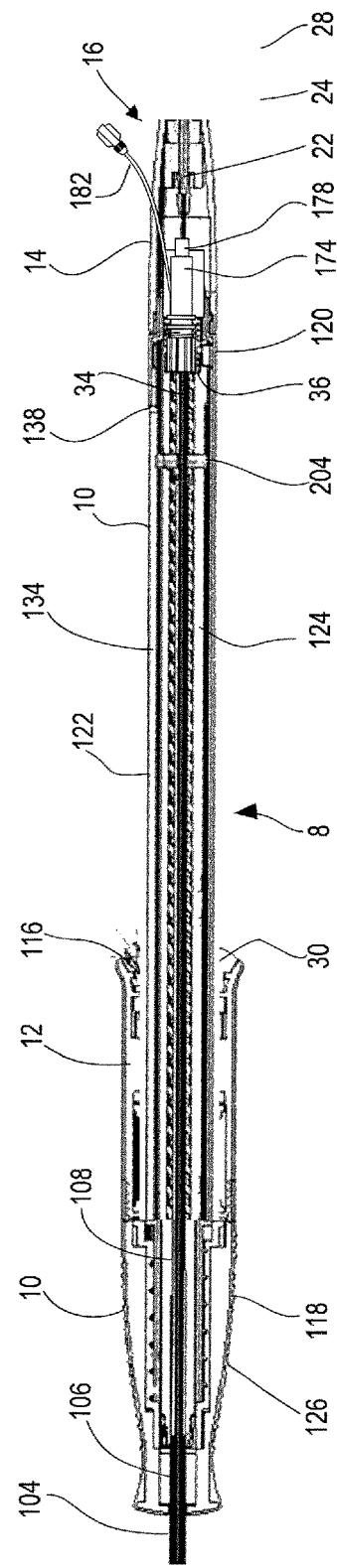
FIG. 9 is a side cross-sectional view of the handle assembly.

As shown generally in FIGS. 8 and 9, the handle assembly 8 includes a first or main handle 10 and second or outer handle 12. The main handle 10 is fixed relative to the delivery device 2. The second handle 12 is disposed on at least a portion of the main handle 10 and is movable longitudinally and/or circumferentially relative to the main handle 10.

Figure 10:
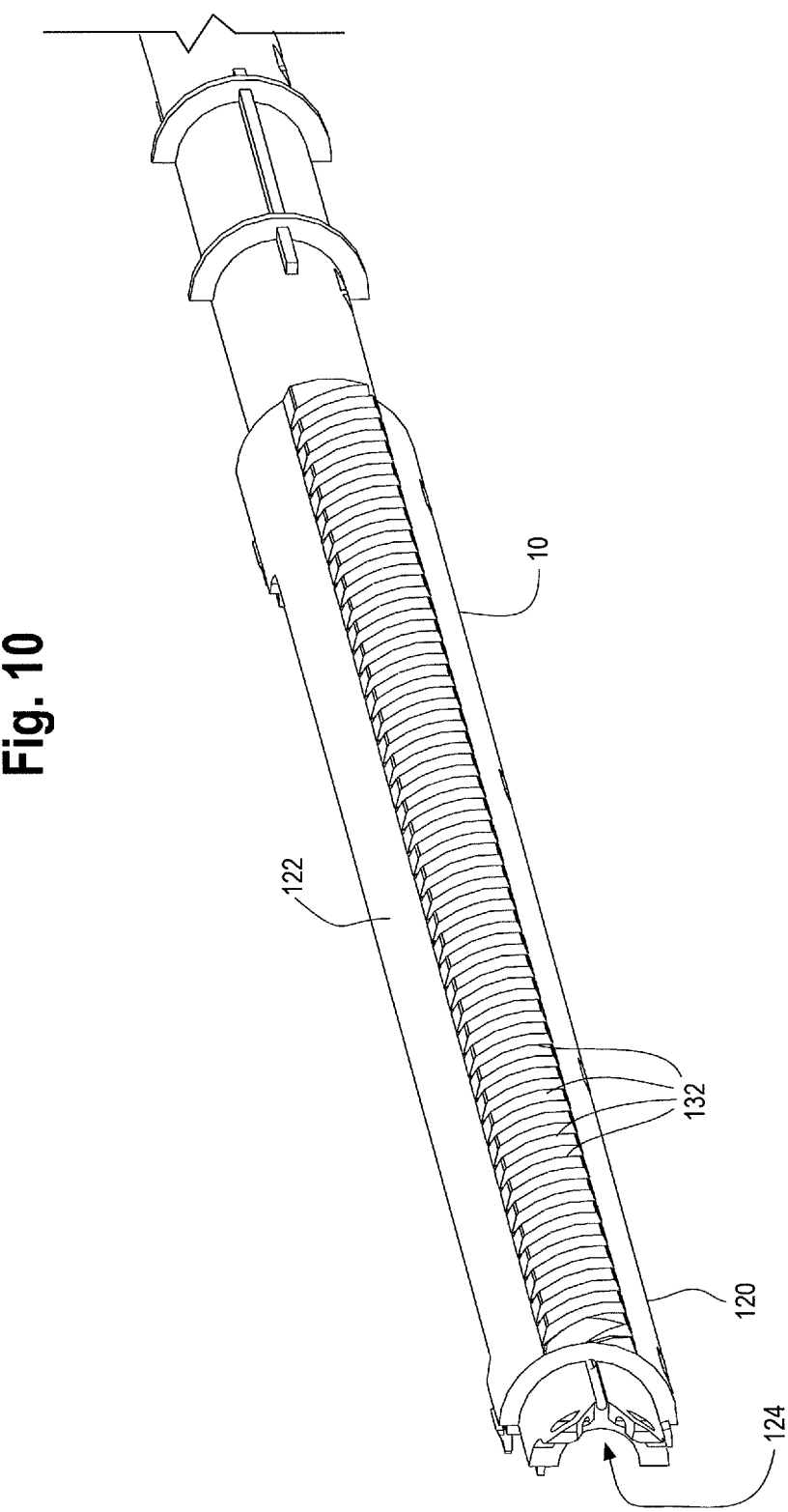
FIG. 10 is a rear perspective view of a portion of the main handle of the handle assembly.

The main handle 10 comprises a proximal end 118 and a distal end 120 with an outer surface or side wall extending there between to form a handle interior 124. As will be described below, the handle interior 124 houses additional mechanical components that make up the handle assembly 8. The main handle 10 may be injection molded as a single unitary structure or alternatively, as shown in FIG. 10, the main handle 10 may comprise upper and lower parts or first and second halves that clam shell, lock, snap-fit or are otherwise securable to each other.

The proximal end 118 of the main handle 10 may include a gripping portion 126 for a physician to grip with one hand while manipulating the second handle 12 (such as during sheath retraction during deployment). The gripping portion 126 of the main handle 10 is preferably ergonomically shaped for user comfort, and may be covered in a layer of softer plastic or rubber or have a gripping surface to ensure a stable grip. As shown in FIG. 2, the gripping portion 126 is a proximal portion of the main handle that may have a greater diameter 128 than the remainder of the main handle 10 which has a reduced diameter portion 130 and extends distally behind the gripping portion 126. It is the reduced diameter portion 130 of the main handle 10 upon which the second handle 12 can longitudinally move.

Figure 11:
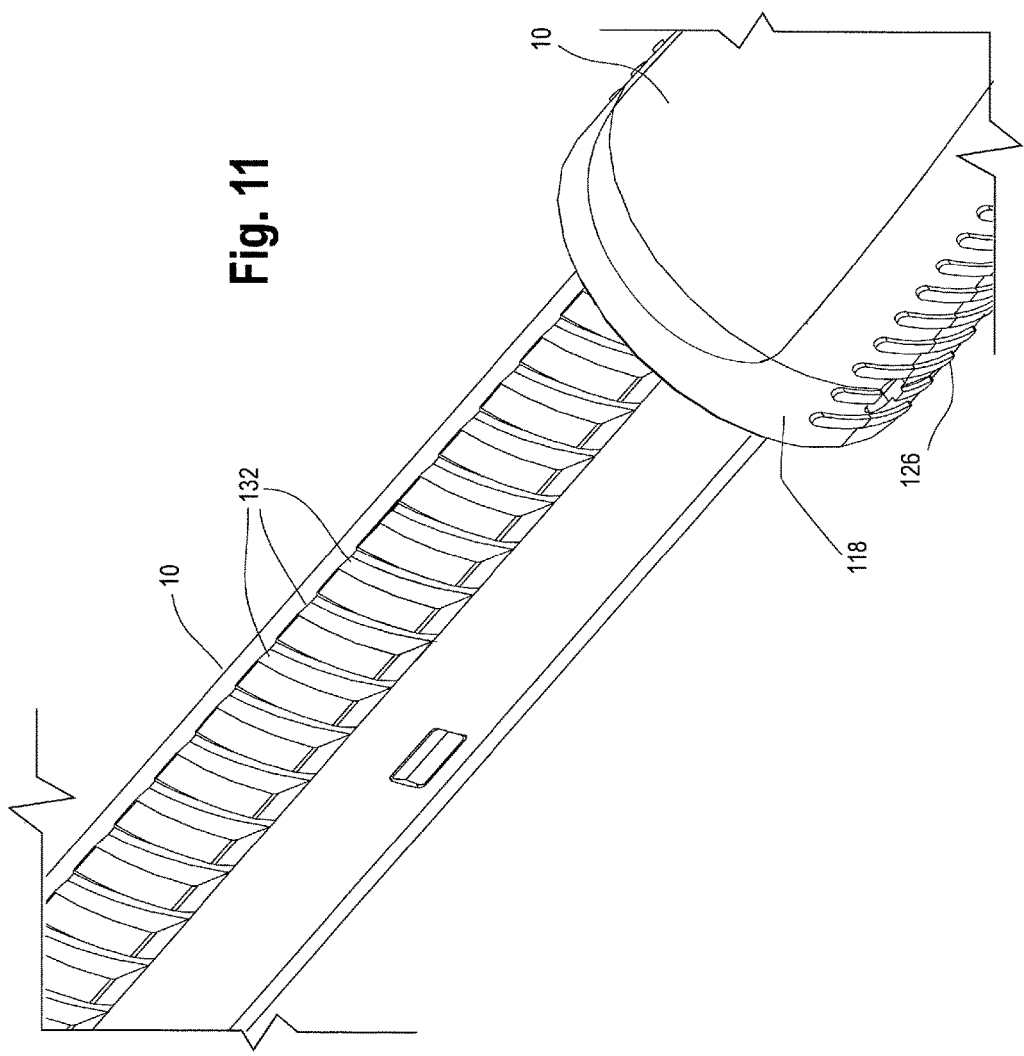
FIG. 11 is a front perspective enlarged view of a portion of the main handle of the handle assembly.
Figure 12:
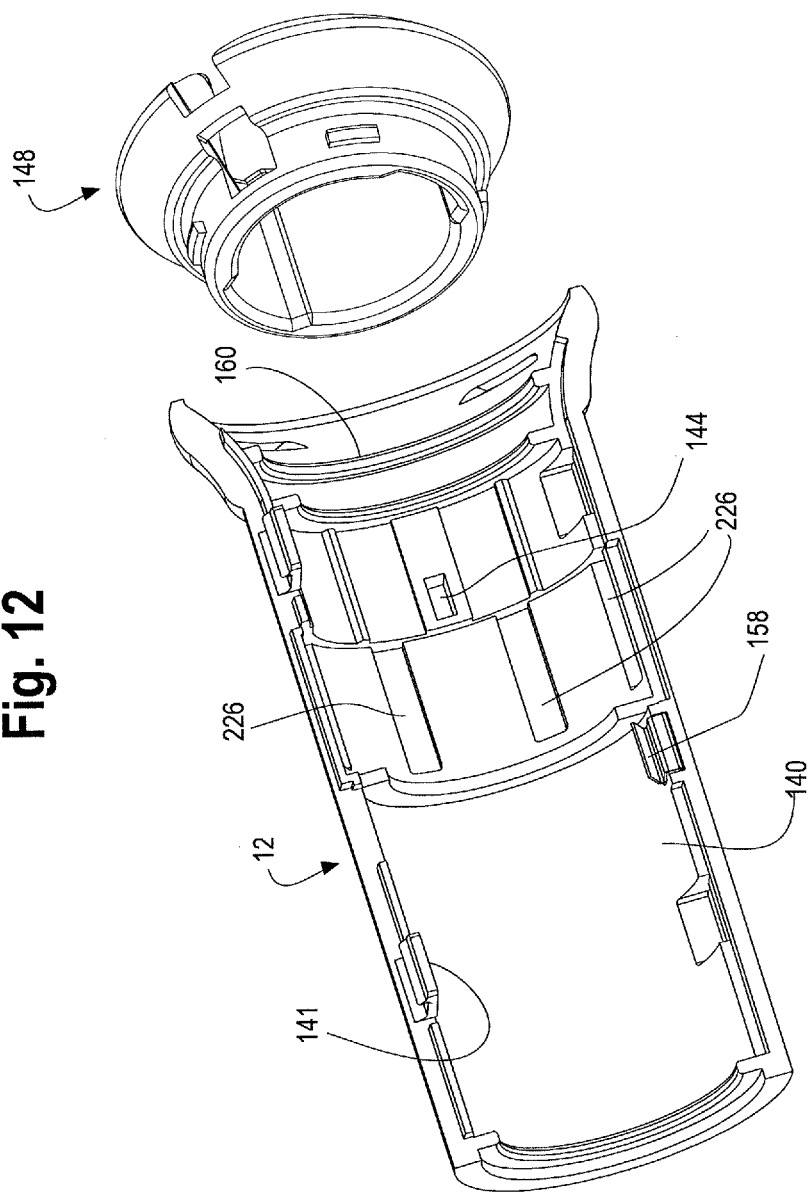
FIG. 12 is an exploded cross-sectional view of the outer rotating second handle and end cap.

At least a portion of the outer surface 122 of the main handle 10 includes partial or full threads 132 along its surface 122 as shown in detail in FIG. 11, which threads 132 extend distally from a location just distal of the gripping portion 126 to the handle end cap 14. A longitudinal slot 134 having a proximal end 136 and a distal end 138 is formed along a portion of the length of the main handle 10, between the gripping portion 126 and the handle end cap 14. As shown in FIG. 8, the second handle 12 is located on the main handle 10. The second handle 12 may be a generally tubular structure that extends at least partially around the outer surface 122 of the main handle 10. The second handle 12 may be injection molded as a single unitary structure or alternatively, as shown in FIG. 12 the second handle 12 may comprise upper and lower parts or halves that clam shell, lock, snap-fit by snaps 141 or are otherwise securable to each other. The second handle 12 may further include an end cap 148. The end cap 148 may consist of two halves which can be attached together by various mechanisms such as snap fit, friction fit, corresponding engageable protrusions or by adhesives. The second handle 12 mechanically engages with the end cap 148 thereby preventing axial/longitudinal movement between the respective two parts but allows the second handle 12 to rotate independently from the end cap 148. In one example, as shown in FIG. 12, one or more protrusions 160, such as a collar, thread or ring on the inner surface 140 of the second handle 12 may be engageable with a correspondingly shaped collar, protrusion, thread or ring on the end cap 148.

The inner surface 140 of the second handle 12 may further comprise one or more structures, which engage with a mechanism such as a nut 142. As previously mentioned, the nut 142 is located within the second handle 12 as shown generally in FIG. 13, where a portion of the second handle 12 has been removed to show the nut 142 in the interior of the second handle 12. In one non-limiting example, as shown in FIG. 12, the second handle 12 may comprise an opening or aperture 144 which engages with one or more radial protrusions 146 on the nut 142 (also see FIGS. 22, 24 and 31-33). As such, at least a portion of the inner surface 140 of the second handle 12 is engaged or otherwise operatively connected with the nut 142. One of skill in the art would recognize that any similar mechanisms or structures that allow the second handle 12 to engage with the nut 142 may be used. As shown in FIGS. 15 and 16, the nut 142 may be a cylindrical or tubular structure that completely encircles a portion of the main handle 10, or the nut 142 may partially cover or surround the main handle 10.

In one example, the nut 142 may be a solid structure, or as shown in FIGS. 16, 31 and 33, a distal end 149 may be a solid structure or ring which encircles a portion of the main handle 10 while a proximal end 150 of the nut 142 may comprise a series of adjacent panels, fingers or flanges that extend proximally from the distal end 149 of the nut 142. The nut 142 may be constructed from a resilient material, including plastics, rubbers, metals, polymers, or a combination thereof. As shown in FIG. 16, the nut is constructed of a resilient material and includes one or more shimstocks 151 that are integrally formed with the nut or alternatively, the shimstocks 151 are separate components that are fitted within a correspondingly shaped channel formed in the nut and then secured to the nut, such as by adhesives or other acceptable attachment mechanisms. The shimstocks 151 are essentially a thin stainless steel flat wire with thickness of about 0.003-0.010 inches may serve as a "skeleton" to the nut.

As will be described in further detail below, the proximal end 150 of the nut 142, including the series of fingers or flanges, may flare radially outwardly in a neutral or relaxed state. (See FIG. 16 and FIG. 33, for example). The proximal end of the nut has a second radially inwardly compressed state, such that the inner surface of the nut 142 is configured to engage with an outer surface 122 of the main handle 10. (See FIG. 31, for example.) The shimstocks 151 help to preserve the shape of the nut and maintain the resiliency of the nut, to help ensure that the proximal end of the nut can move from the inwardly compressed state to the radially outwardly flared state. In one non-limiting example, the shimstocks 151 help to safeguard from the effect of ageing of plastic or other resilient materials from which the nut 142 may be constructed by preserving resiliency and the tendency for the nut 142 to flare radially outwardly. If the nut loses its elasticity or resiliency, the internal threads on the nut 142 may not fully separate or disengage from the external threads 132 of main handle 10. The shimstocks 151 facilitate disengagement of the nut 142 from the main handle 10 when necessary or desired as described in detail below.

Figure 14:
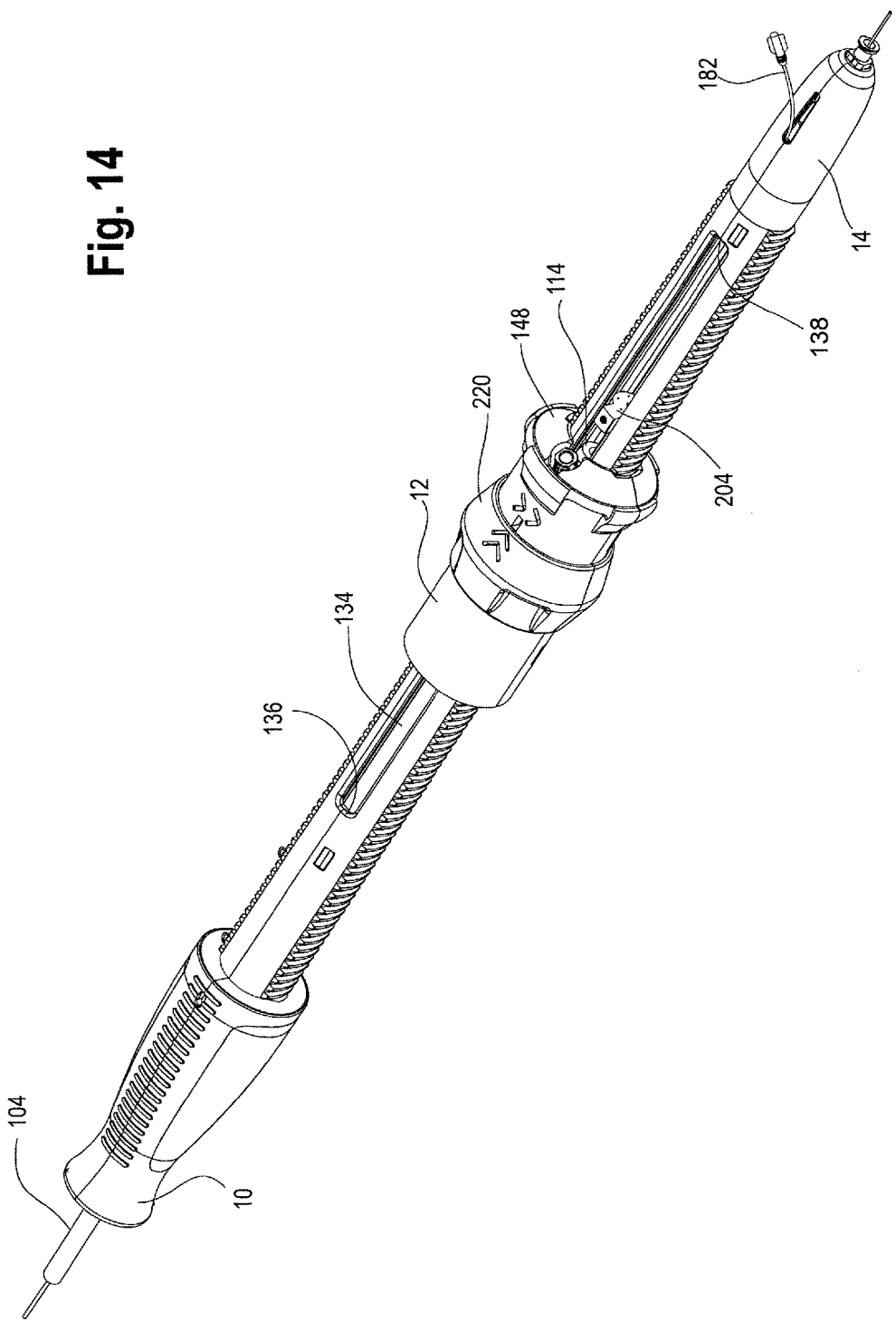
FIG. 14 is a perspective view of the handle assembly with the second handle moved distally relative to the main handle to at least partially retract the sheath.
Figure 40:
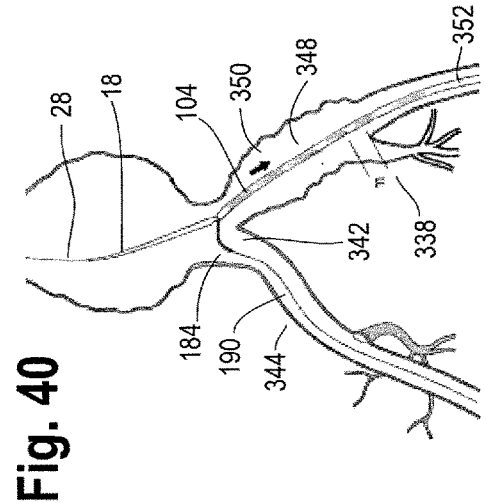
FIG. 40 illustrates the initiation of distal retraction of the sheath and the access sheath removed.
Figure 41:
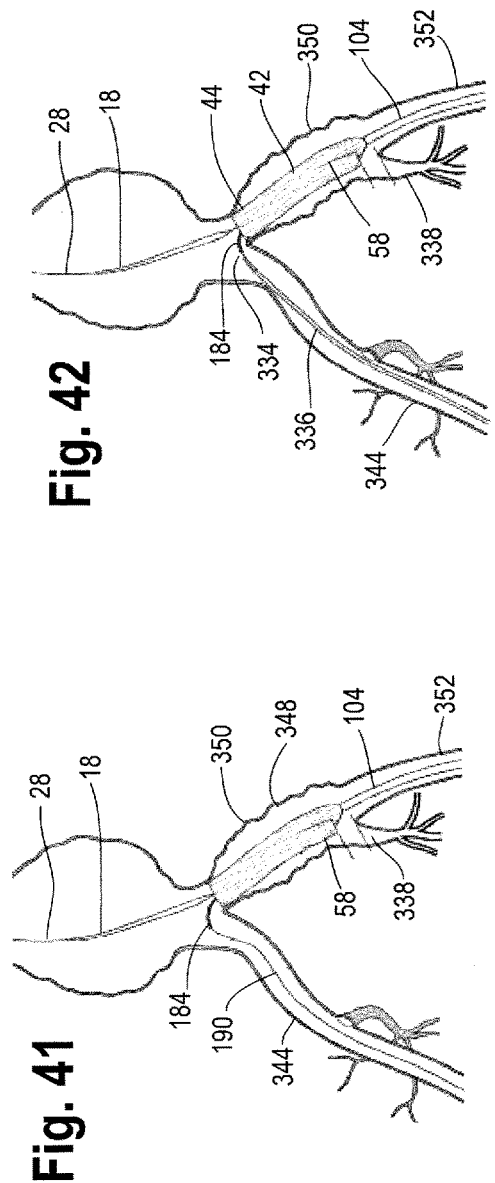
FIG. 41 illustrates the sheath retracted to expose the proximal end and side arm of the stent graft.

The second handle 12 may be rotated to move it from its first proximal most position on the main handle 10 (as shown in FIGS. 1, 8 and 15) to various intermediate positions (such as in FIGS. 14, 21 and 22, for example) located between the proximal and distal ends 136, 138 of the longitudinal slot 134 formed in the main handle 10. Distal movement of the second handle 12 relative to the main handle 10 requires rotation of the second handle 12 when the inner surface 152 of the nut 142 within the second handle 12 is threadedly engaged with the outer surface 122 of the main handle 10. In other words, this threaded engagement necessitates rotation of the second handle 12 to impart longitudinal movement of the second handle 12 relative to the main handle 10. Rotation of the second handle 12 may be desired so as to provide more control and accuracy to the sheath retraction and stent graft placement and deployment (as shown in FIGS. 40 and 41, for example).

Figure 13:
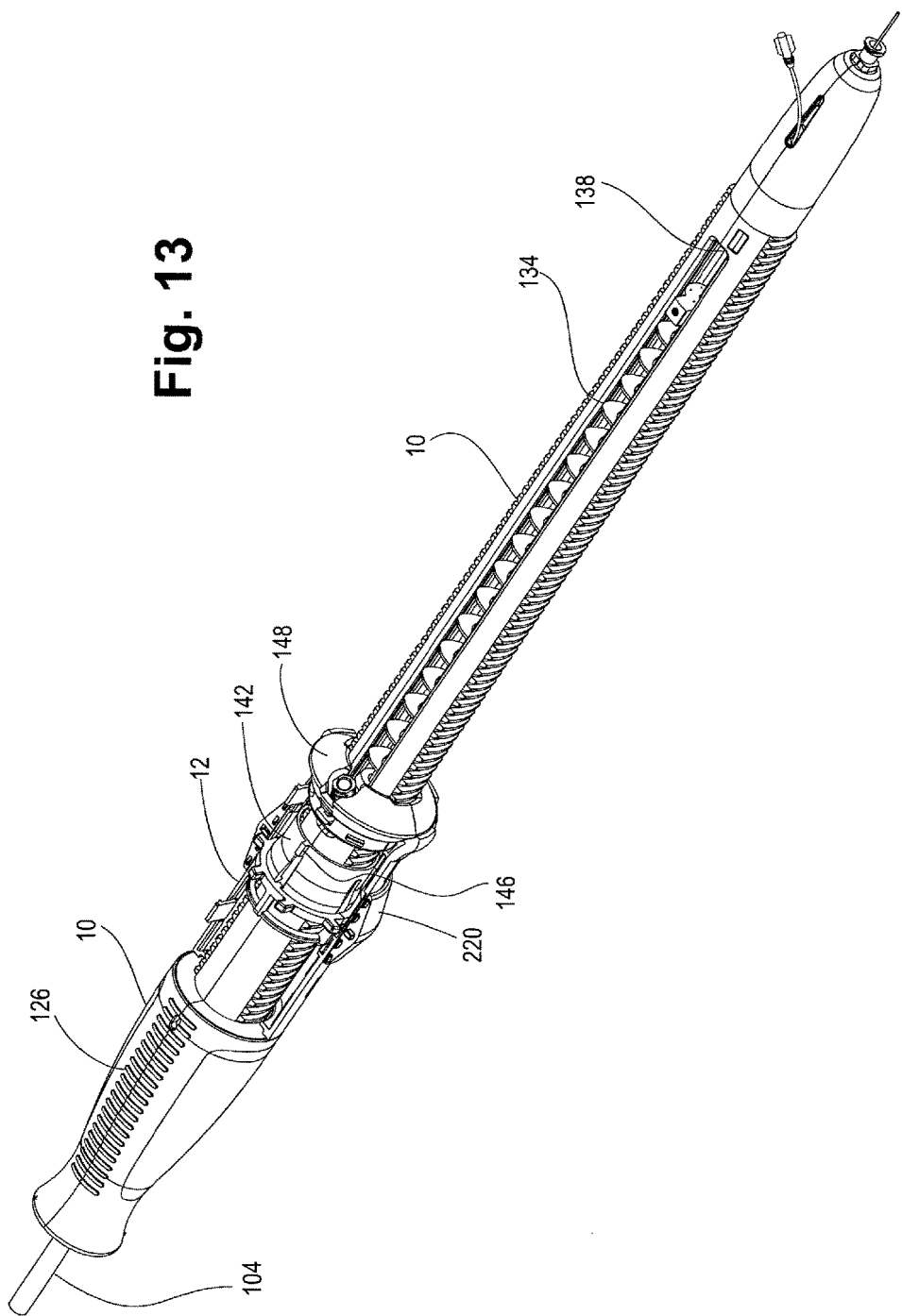
FIG. 13 is a perspective view of the handle assembly with a portion of the second handle removed.

FIGS. 13 and 15 are perspective views of the handle assembly 8 shown with a portion of the second handle 12 removed, showing the second handle 12 in a proximal most position on the main handle 10. A ratcheted collar 154 is positioned under the second handle 12. The ratcheted collar 154 may fully or partially surround the main handle 10. As shown in FIG. 15, the ratcheted collar 154 extends distally from the gripping portion 126 of the main handle 10. The ratcheted collar 154 may be molded from a single unitary piece of material or may be multiple separately molded pieces (i.e., a collar portion 154a and a ratchet portion 154b) which are attached together such as by welding or glue. The ratcheted collar 154 may have one or more protrusions or teeth 156 that allow only for unidirectional rotation of the second handle 12. For example, one or more protrusions formed on the inner surface 140 of the second handle 12, or, alternatively a shim 158 positioned in a slot on the inner surface 140 of the second handle 12, as shown in FIG. 12, engage with the ratcheted collar 154, so that the second handle 12 can rotate about the main handle 10 in one direction, while rotation of the second handle 12 about the main handle 10 in the opposite direction is prevented.

The ratcheted collar 154 is preferably shaped so that it does not rotate relative to the main handle 10, but which allows the ratcheted collar 154 to slide longitudinally relative to the main handle 10. For example, the cross-sectional shape of the ratcheted collar 154 may be oblong or polygonal, have one or more flat sides or be irregularly shaped so that rotation of ratcheted collar 154 is prevented when the second handle 12 is rotated about the main handle 10, but which allows the ratcheted collar 154 to move longitudinally along the main handle 10 as the second handle 12 is moved distally by the user. It will be appreciated that the components of the handle assembly 8, including the second handle 12, may be designed to rotate in any particular direction, however, as described herein for exemplary purposes, the ratcheted collar 154 is configured to permit clockwise rotation of the second handle 12 and prevent counter-clockwise rotation.

Figure 26:
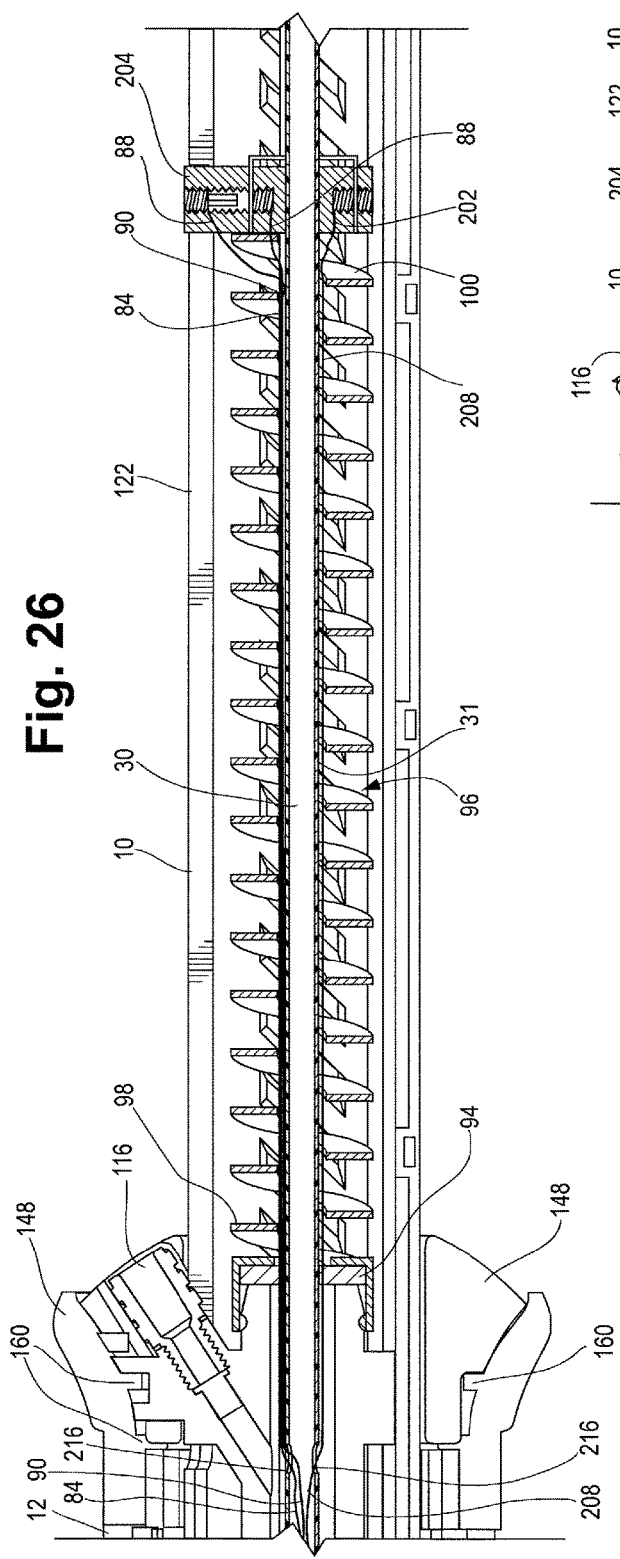
FIG. 26 is an enlarged side cross-sectional view of the handle assembly illustrating the trigger wires extending proximally from the trigger wire knob, through the conduit provided by the expanded spring and into the lumen of the positioner.

Before use of the delivery device 2 and when the delivery device is tracked to a desired location within a patient's body, the second handle 12 is disposed in a first or proximal-most position on the main handle 10 and the stent graft 42 at the proximal end 4 of the delivery device 2 is fully sheathed and held in a radially inwardly contracted condition as shown in FIGS. 1, 2 and 34. More specifically, with the stent graft 42 fully sheathed, the series of stents 50 on the main tubular body 62 as well as the stents 72 on the side arm 58 are held in a radially inwardly contracted condition. As the second handle 12 is rotated to move it distally along the main handle 10, the protrusion 160 (such as a collar or ring on the inner surface 140 of the second handle 12) engages with a protrusion on the end cap 148 as shown in FIGS. 12 and 26. As mentioned above, the second handle 12 can rotate freely and independently of the end cap 148. The longitudinal slot 134 formed in the main handle 10 accommodates the sheath flush port 116 on the sheath connector 108, such that as the second handle 12 is moved distally relative to the main handle 10, the sheath flush port 116 can slide distally along with the sheath connector 108 and the second handle 12 through this longitudinal slot 134 formed in the main handle 10 as shown generally in FIG. 14.

As the second handle 12 rotates and moves distally along the main handle 10, the end cap 148 is pushed distally, which in turn pushes the sheath connector 108 distally, thereby also pulling the sheath 104 distally, to expose a proximal end 44 of the stent graft 42. Further retraction of the second handle 12 may also facilitate the retraction of the trigger wires as well as expose the distal end 48 of the stent graft 42, as will be described further below. In other words, when the second handle 12 is in the proximal most position on the main handle 10 as shown in FIGS. 1, 2 and 8, the stent graft 42 is fully covered by the retractable sheath 104 at the stent graft retention region 16 of the device 2, and the trigger wires retain the stent graft 42 in a radially-inwardly constrained delivery configuration against the inner cannula 22. The trigger wires cannot be retracted in order to release the stent graft 42 from a radially inwardly constrained delivery configuration until an appropriate stage of deployment (i.e., after the second handle 12 has been retracted distally for a pre-determined distance, thereby withdrawing the sheath 104 a sufficient distance to expose at least the proximal end of the stent graft and the side arm 58).

Figure 17:
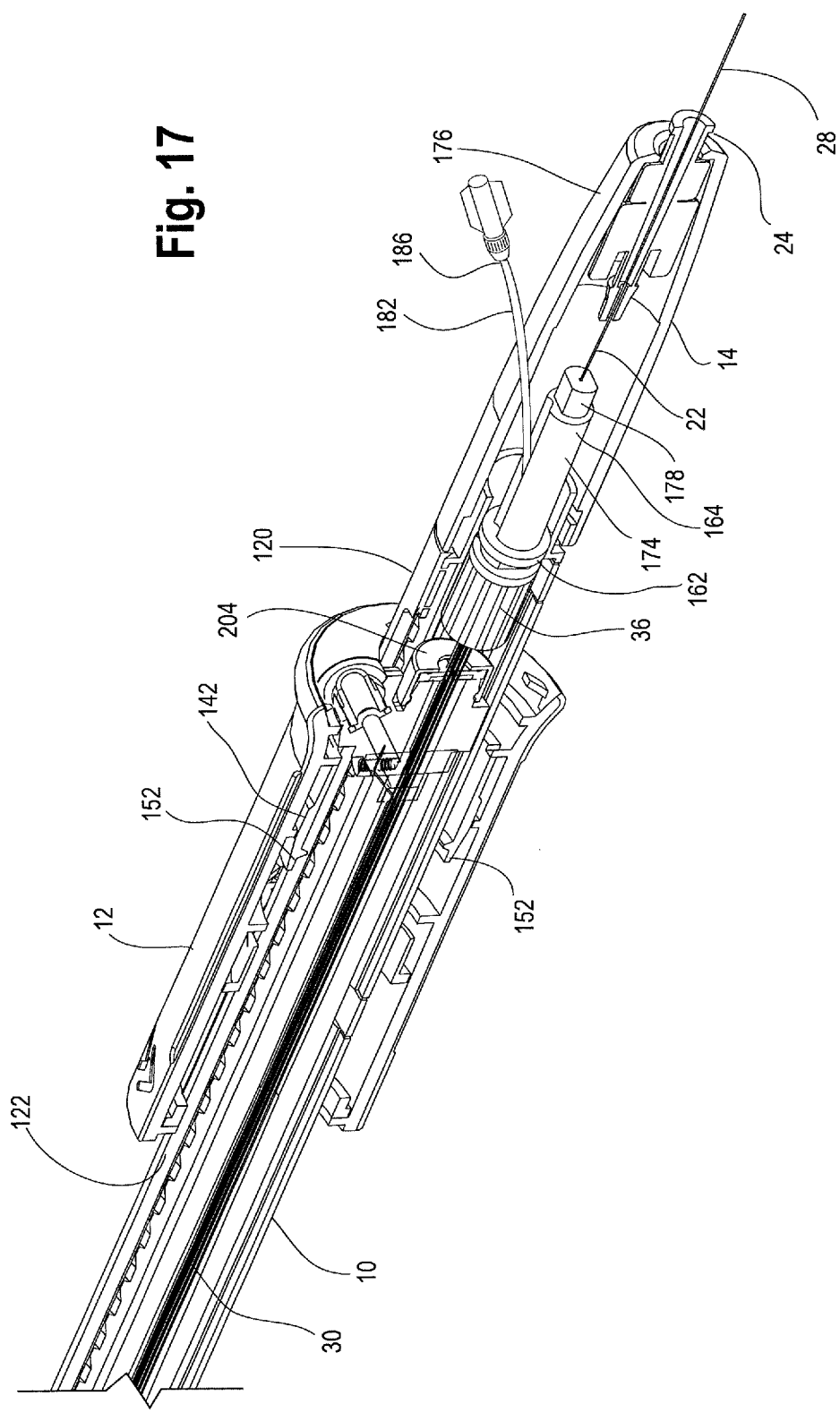
FIG. 17 is a rear perspective cross-sectional view of the distal end of the handle assembly.
Figure 18:
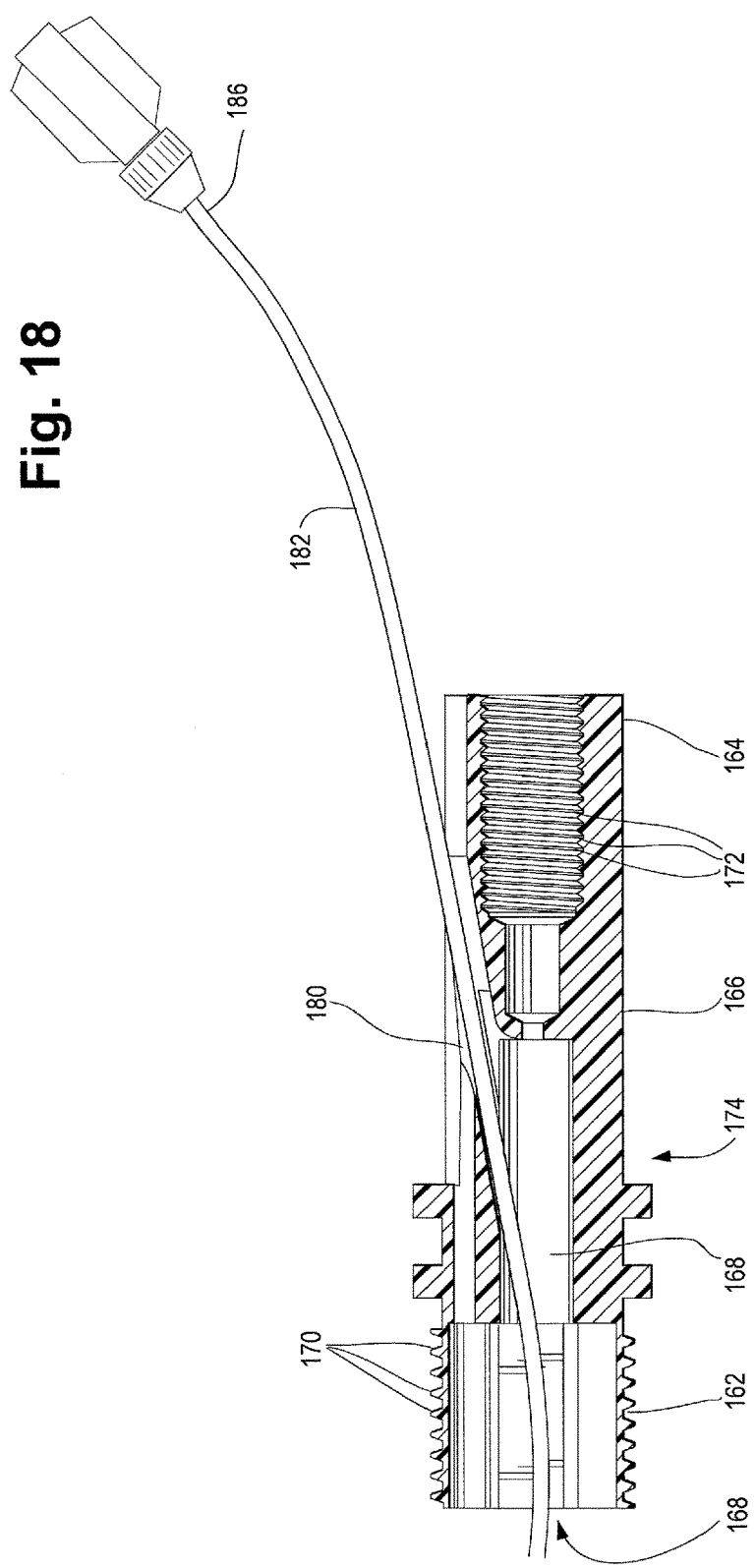
FIG. 18 is a side cross-sectional view of a catheter extending through one example of a catheter hub.
Figure 25:
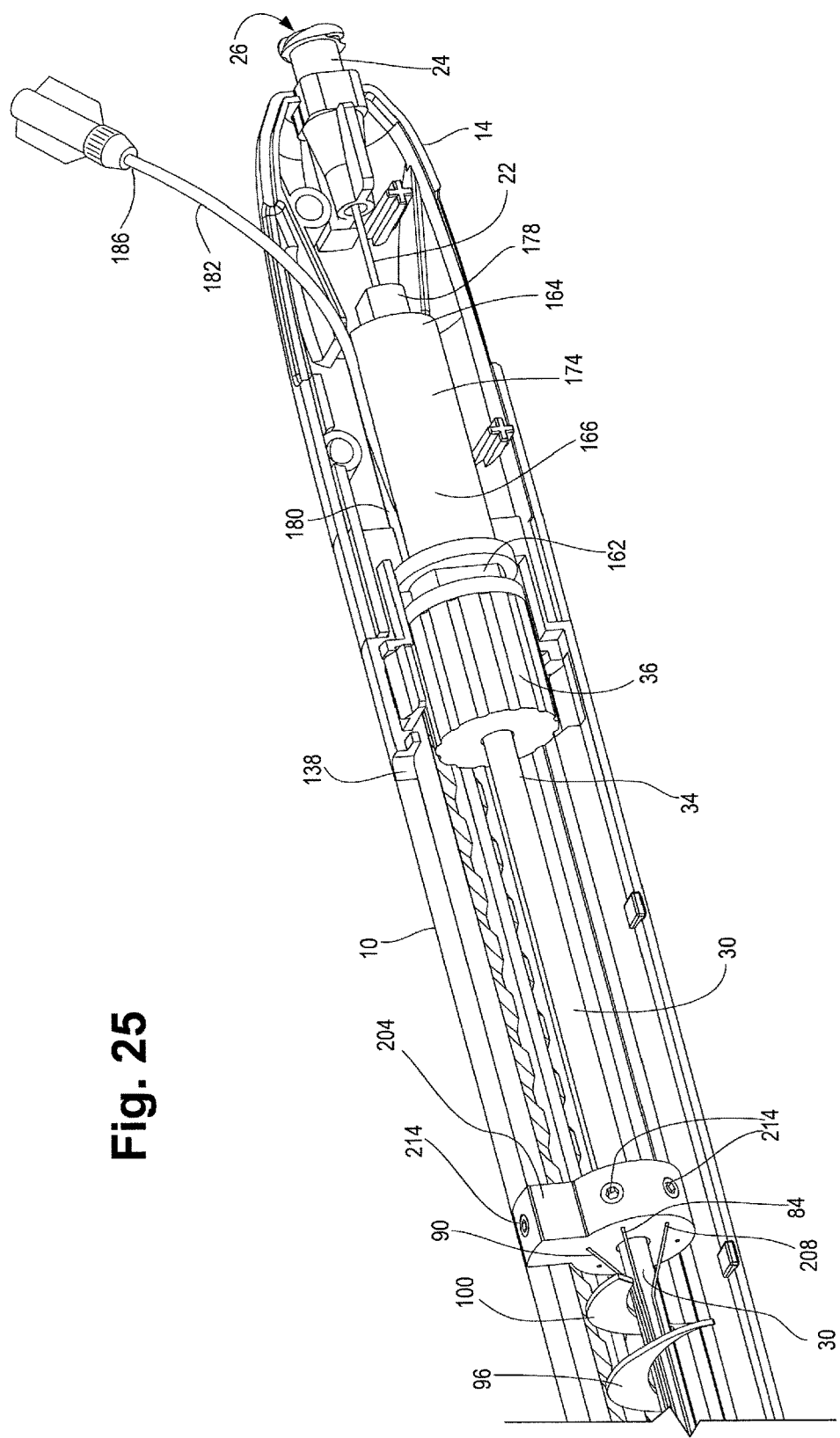
FIG. 25 is an enlarged partial sectional view of one example of a distal end of the handle assembly.

As depicted generally in FIGS. 17, 18 and 25, a catheter hub 174 is disposed at least partially within the end cap 14 at the distal end 120 of the main handle 10. The back end cap 14 may be a single structure or multiple parts or halves snap-fitted together and into engagement with the distal end 120 of the main handle 10. End cap 14 may have a distal taper 176 and may be removable or split open by the user should the need arise, such as in an emergency "bailout" procedure in the event that one or more components of the handle assembly 8 fail during deployment, thus allowing the user to remove the end cap 14 and access the handle interior 124, to manually perform certain deployment steps described in further detail below. The inner cannula 22 extends distally through the back end cap 14 to the distal flush hub 24, as can be seen in FIG. 17.

With reference to FIGS. 17 and 25, the catheter hub 174 is disposed circumferentially around the inner cannula 22, and secured in place, such as by the pin vise 178, although other suitable mechanisms for attaching the inner cannula 22 to the catheter hub 174 are also contemplated, including adhesives, welding and the like, for example. As shown in detail in FIG. 18, the catheter hub 174 has a proximal end 162 and a distal end 164, an outer surface 166 and a lumen 168 extending between the proximal and distal ends. The proximal end 162 of the catheter hub 174 has outer threads 170 that are configured to mate with correspondingly shaped threads (not shown) formed within the stationary collar 36. The distal end 164 of the catheter hub 174 comprises inner threads 172 that are configured to mate with correspondingly shaped threads (not shown) formed on the pin vice 178. As such, the pin vice 178 can be inserted into and secured to the distal end 164 of the catheter hub 174, thereby attaching the catheter hub 174 and the inner cannula 22.

As shown in FIG. 18, a channel or groove 180 extends proximally from the distal end 164 along a portion of the outer surface 166 of the catheter hub 174. About one-third to one-half the distance from the distal end 164 of the catheter hub 174, the channel 180 that is formed in the outer surface 166 of the catheter hub 174 angles or slants downwardly and towards the lumen 168 of the catheter hub 174 and intersects with the lumen. As will be discussed in greater detail below, a catheter 182 having a proximal end 184 a distal end 186 and a lumen extending there between extends along the groove 180 formed in the outer surface 166 of the catheter hub 174, through the lumen 168 of the catheter hub 174 and proximally through the lumen of the positioner 30. The catheter 182 exits from the lumen of the positioner 30 at the proximal end 32 of the positioner (where the proximal end 32 of the positioner is located just distal to the distal end 48 of the stent graft 42) and the catheter 182 further extends along the outer surface of the nose cone dilator 18. The proximal end 184 of the catheter 182 extends through and within one or more grooves 188 formed in the nose cone dilator 18.

The groove 188 formed in the nose cone dilator 18 may be a longitudinal groove, or it may comprise other configurations, such as that shown in FIGS. 5, 6, 19 and 20 where the groove 188 in the nose cone dilator 18 is substantially straight near the distal end 82 of the nose cone dilator 18 and then curves around substantially perpendicularly to the longitudinal axis. The catheter 182 extends through the groove 188 formed in the nose cone dilator 18 and conforms to the shape and configuration of the groove 188. As shown in FIGS. 19 and 20, the proximal end 184 of the catheter 182 lies substantially straight along the straight longitudinal portion at the distal end of the groove 188 and the catheter 182 then bends to conform to the bend or curve in the proximal portion of the groove 188. As FIGS. 20 and 38 show, the lumen of the catheter 182 is sized to accommodate a guide wire 190 there through.

With the sheath 104 retracted to expose the proximal end 44 of the stent graft 42, the user may continue to rotate the second handle 12 to further move the second handle 12 distally along the main handle 10, thus further retracting the sheath 104 and exposing more of the main body 62 of the stent graft 42 (and, depending on the length and location of the side arm 58 on the main body 62) also expose at least a portion of the side arm 58 as shown in FIG. 41. In cases where the side arm 58 is relatively short as shown in FIG. 4, the second handle 12 may only need to be moved distally a relatively short distance along the main handle 10 to fully expose the side arm 58. On the other hand, in cases where the side arm 58 is relatively longer (as shown in FIG. 3) the second handle 12 must be moved further distally on the main handle 10 in order to fully un-sheath and expose the side arm 58.

Figure 27:
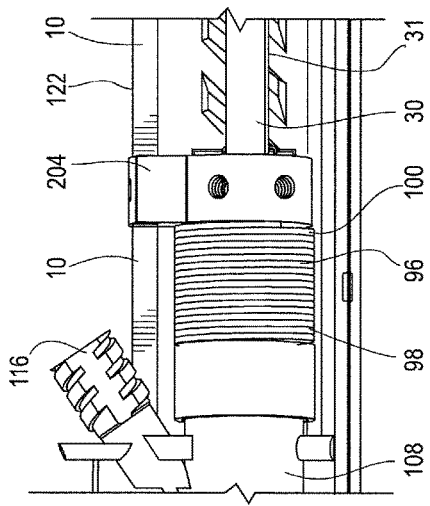
FIG. 27 illustrates the second handle moved distally towards the trigger wire knob to compress the spring.

The second handle 12 may continue to move distally until the distal end 14 of the sheath connector 108 within the second handle 12 and/or the end cap 148 touches, meets, abuts or is otherwise adjacent to a trigger wire release mechanism 204 located within the main handle interior 124, as shown in FIGS. 21 and 27. The user may feel a slight resistance which signals that the sheath connector 108 has reached the trigger wire release mechanism 204. Other visual or mechanical signals may also be present on the delivery device 2 and/or handle assembly 8 to indicate to the user to stop rotating the second handle 12 (to thereby stop further distal movement of the second handle 12 along the main handle 10) including visual cues provided by desired imaging modality (i.e., by fluoroscopy, MRI, 3D or other imaging techniques). At this point, in one non-limiting example, distal movement of the second handle 12 relative to the main handle 10 has moved the sheath connector 108 distally, thereby retracting the sheath 104 a sufficient travel distance 206 such that the proximal end 44 of the stent graft 42 and at least a portion of the side arm 58 has been exposed. The distal end of the stent graft 42, however, may still be sheathed, as shown in FIG. 41.

Figures 23, 24:
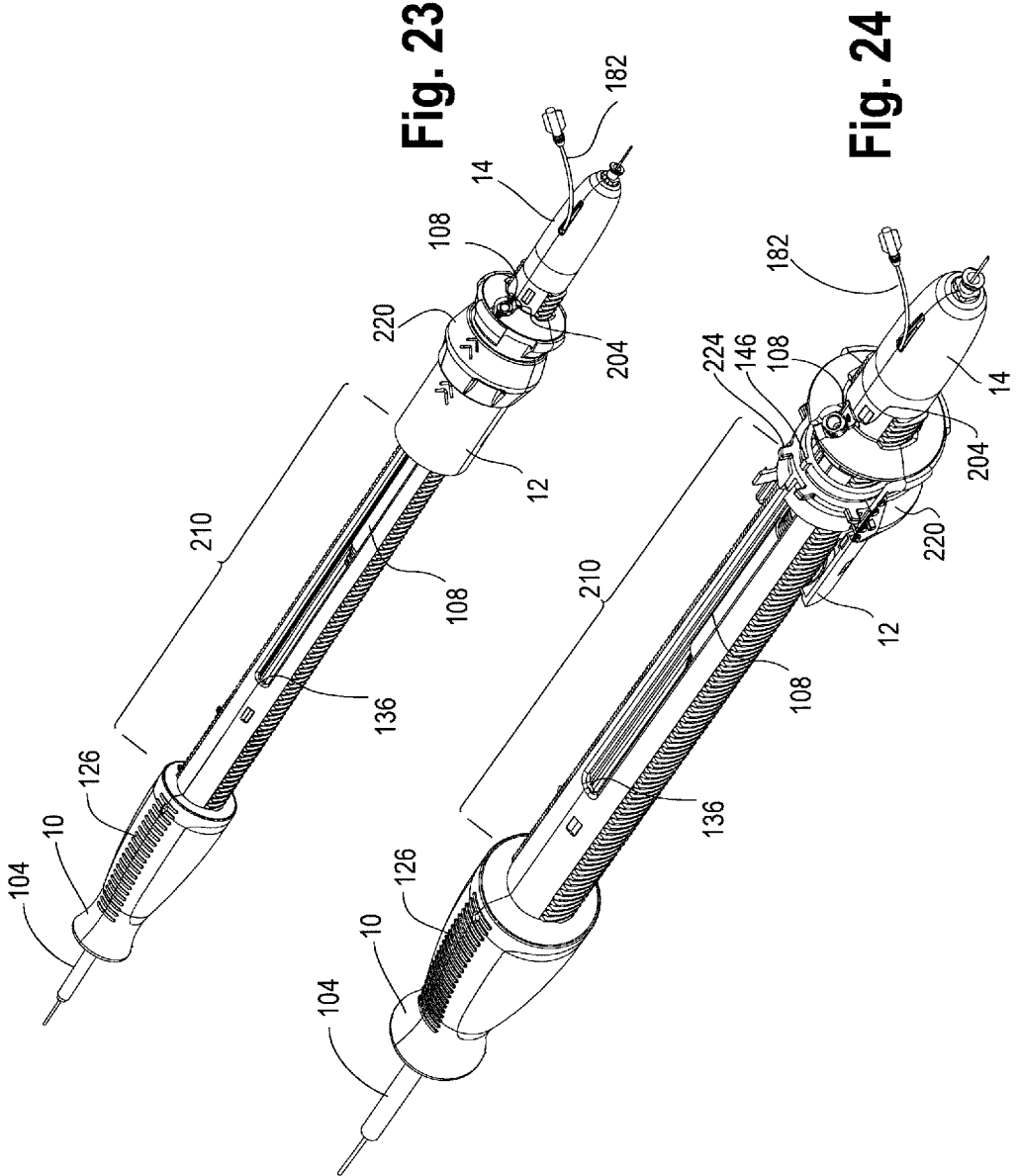
FIG. 23 is a perspective view of the handle assembly with the second handle fully retracted relative to the main handle.
FIG. 24 is a perspective view of the handle assembly of FIG. 23 with a portion of the second handle and outer ring removed to illustrate the sleeve in a distal position and the nut disengaged from the main handle.

At this stage, the user may continue to move the second handle 12 distally to a final or distal-most position on the main handle 10 as shown in FIGS. 23 and 24 to further retract the sheath 104 and expose the distal end 48 of the stent graft 42, while and simultaneously releasing of the proximal trigger wires 84, 90 as well as any additional attachment mechanisms, including one or more distal trigger wires 208 that may be in place to releasably couple the distal end of the stent graft 42 from the inner cannula 22.

This final distal movement of the second handle 12 to a position on the main handle 10 as shown in FIGS. 23 and 24 may be accomplished by the user continuing to rotate the second handle 12 relative to the main handle 10 as described above, where rotation of the second handle 12 causes the second handle 12 to travel distally in a longitudinal direction along the main handle 10. Alternatively, rather than continuing to rotate the second handle 12 to move it distally, the user has the option to implement a "quick release" protocol in order to retract the second handle 12 distally without rotation, as will be described in further detail below.

The distance of travel of the second handle 12 relative to the main handle 10 to this final or distal-most position is identified as reference number 210 in FIGS. 23 and 24. In other words, distal movement of the second handle 12 from an intermediate position in FIGS. 21 and 22 to the distal most position in FIGS. 23 and 24 causes the sheath connector 108 to retract distally (thereby retracting the sheath 104 distally) to expose the distal end 48 of the stent graft 42. At the same time, the distal end or end cap 148 of the second handle 12 and/or the distal end 114 of the sheath connector pushes against the trigger wire release mechanism or knob 204 located within the main handle 10 as shown in FIG. 27. As shown in FIGS. 25 and 26 and described above, the trigger wire release mechanism 204 is a ring that is slidably disposed over the positioner 30. One or more distal trigger wire(s) 208 extend proximally from the trigger wire release mechanism 204 to the distal end of the stent-graft 48 as described further below and shown in FIGS. 26 and 28-30. The distal trigger wire(s) 208 have a proximal end 200 and a distal end 202. The distal end 202 of the distal trigger wire 208 may be secured to, connected or otherwise attached to the trigger wire release mechanism 204 as shown in FIG. 25.

In one example, the positioner 30 provides a conduit for the proximal trigger wires 84, 90 and/or the distal trigger wire(s) 208 to extend from the trigger wire release mechanism 204 in the main handle 10 to the proximal end and distal end 44, 48, respectively of the stent graft 42. As shown in FIG. 26, the distal end 202 of trigger wire 208, along with the distal ends 88 of the proximal trigger wires 84, 90 may be secured to the trigger wire release mechanism 204 by one or more set screws 214, although other attachment mechanisms may be used including adhesives, welding, crimping or a combination thereof. The proximal trigger wires 84, 90 and the distal trigger wire 208 then extends proximally from the trigger wire release mechanism 204 and run along the outer surface 31 of the positioner 30. A coil or spring 96 that is coaxial with and extends around and along the outer surface 31 of the positioner 30 retains the trigger wires 84, 90, 208 against the outer surface 31 and provides a conduit through which the trigger wires 84, 90, 208 can extend. In other words, the proximal trigger wires 84, 90 and the distal trigger wire 208 are held between the outer surface 31 of the positioner and the inner surface of the coil 96.

As FIG. 26 shows, the coil 96 has a proximal end 98 that is adjacent to and/or abuts the distal end cap 148 of the outer rotating handle 12 and/or the distal end 114 of the sheath connector 108. A distal end 100 of the coil 96 is adjacent to and/or abuts the trigger wire release mechanism 204. The coil 96 may be constructed of various resilient materials, for example, stainless steel or other metals or alloys, plastics, rubbers and/or polymers, and in one example, the coil 96 is constructed of nylon. The coil 96 may be biased in an expanded position. As shown in FIG. 26, the proximal trigger wires 84, 90 and the distal trigger wire 208 extends proximally beyond the proximal end 98 of the coil 96 and into the end cap 148 of handle 12. Within the back end cap 148 is a hemostatic valve 94 or seal, such as an "0" ring or silicone disc to maintain hemostasis within the main handle 10 and to prevent leakage or back flow of fluids around the positioner 30, or in other words, prevents leakage between the outer diameter of the positioner 30 and the sheath connector 108. The trigger wires 84, 90, 208 extend through the hemostatic valve 94 and enter into the positioner 30 through one or more openings, holes or apertures 216 formed in the positioner 30 as shown in FIG. 26. The trigger wires 84, 90 and 208 further extend proximally through the conduit provided by the lumen of the positioner 30 to the stent graft 42.

The distal trigger wire(s) 208 may be directly or indirectly attached to the distal end 48 of the stent graft 42. For example, the distal trigger wire 208 may engage a suture loop 209 which is attached to the distal end 48 of the stent graft 42 as shown in FIG. 28. Alternatively, the distal trigger wire 208 may be woven directly through or removably attached to the graft material 52 or may be woven around or over one or more stents 50 at the distal end of the graft 42 as shown in FIGS. 29 and 30. Other suitable attachment methods or mechanisms may be used to removably attach the distal trigger wire 208 to the distal end of the stent graft 42 as would be recognized by one of skill in the art.

As FIGS. 21-24 illustrate, distal movement of the second handle 12 pushes or drives the trigger wire release mechanism 204 distally with it, thereby pulling the one or more distal trigger wires 208 in a distal direction. More specifically, as the second handle 12 is moved distally along the main handle 10, the coil 96 becomes compressed as seen in FIG. 27. When the coil 96 has become completely compressed, it serves as a spacer between the distal end 114 of the sheath connector 108 (and/or the distal end cap 148 of handle 12) and the proximal facing surface of the trigger wire release mechanism 204. At this stage, as the outer handle 12 continues to move distally backwards by the user, the distal end 100 of the coil 96 will simultaneously push distally backwards on the trigger wire release mechanism 204. As the trigger wire release mechanism 204 is pushed distally backwards, the proximal ends 86 of the proximal trigger wires 84, 90 and the proximal end 200 of the distal trigger wire 208 will be retracted and released from the respective proximal end 44 and distal end 48 of the stent graft 42 (i.e., the proximal and distal trigger wires 84, 90, 208 are retracted and released from the stent graft 42, such as by becoming disengaged from the graft material 52, disengaged from the suture loop 209 and/or disengaged from one or more stents 50 of the stent graft). Distal movement of the second handle 12 ceases upon second handle 12 reaching the distal end 138 of the longitudinal slot 134 formed in the main handle 10 and/or when the trigger wire release mechanism 204 abuts or contacts the stationary collar 36 at the distal end 120 of the main handle 10 as shown in FIGS. 23 and 24.

The steps of a quick release procedure are now generally described. As set forth above, second handle 12 can rotate about the longitudinal axis of the main handle 10 to move the second handle 12 distally to an intermediate position on the main handle, such as that shown in FIG. 21, thus retracting the sheath 104 to expose the proximal end 44 of the stent graft 42, the main body 62 and the side arm 58 as shown in FIG. 41. The threaded engagement between the inner surface 152 of the nut 142 and outer surface 122 of the main handle 10 necessitates rotation to impart longitudinal movement of the second handle 12 relative to the main handle 10. The user may continue to rotate the second handle 12 to move it distally to further retract the sheath 104 to expose the distal end 48 of the stent graft 42 and release the trigger wires 84, 90 from the proximal end 44 of the stent graft and release the trigger wire 208 from the distal end 48 of the stent graft 42 during deployment. However, as an alternative, the quick release procedure may be employed at this stage of deployment, if desired, in order to further retract the sheath 104 to expose the distal end of the stent graft 42 and to simultaneously release the trigger wires 84, 90, 208 without having to rotate the second handle 12 relative to the main handle 10.

More specifically, instead of rotating the second handle 12 to move it distally relative to the main handle 10, the quick release procedure provides the user the ability to slide the second handle 12 freely along the main handle 10 in a straight pull-back motion, so that the second handle 12 can simply slide longitudinally along the main handle 10 in a continuous smooth non-rotating motion. This provides several advantages, including, for example, the user being able to retract the second handle 12 more quickly and without rotation to complete sheath retraction and trigger wire removal. It also facilitates a final stage of a deployment procedure once the entire stent graft 42 is deployed, allowing the user to re-sheath or recapture at least a portion of the nose cone dilator 18 within the sheath 104 for removal of the device 2 from a patient's body as shown in FIG. 51 and described in further detail below.

In the first steps of the quick release procedure, the user can firmly grip the gripping portion 126 of the main handle 10 with one hand while pulling back on an outer handle or ring 220 located on the second handle 12 with the other hand as FIG. 21 shows to "release" or disengage the second handle 12 from the main handle 10, thus allowing the second handle 12 to slide freely along the main handle 10 without rotation in a straight pull-back motion.

More specifically, as shown in FIGS. 31 and 33, the nut 142 located within the second handle 12 extends at least partially circumferentially around at least a portion of the main handle 10. As shown in one example in FIG. 31, the inner surface of the nut 142 is engaged with threads 132 on the outer surface 122 of the main handle 10 by a threaded engagement, although other mechanisms may be used to provide engagement between the nut 142 and the main handle 10. With the inner surface 152 of the nut 142 engaged with the outer surface 122 of the main handle 10, the second handle 12 must be rotated in order to move the second handle 12 distally along the main handle 10 (such as during the previously-described steps of moving the second handle 12 distally to facilitate sheath retraction and proximal stent deployment.)

As shown in FIGS. 31 and 32, a sleeve 222 extends at least partially circumferentially over and/or around the nut 142, or alternatively, the sleeve 222 may completely surround or enclose a portion of the outer surface of the nut 142. In one non-limiting example, the sleeve 222 may be a curved, arcuate and/or semi-circular structure that is positioned about the outer surface of the nut 142, as shown in FIG. 32. The outer surface of the sleeve 222 may have one or more radially outwardly extending protrusions 224 that extend through one or more openings or slots 226 formed in the second handle 12 (see FIG. 12) so as to engage with an opening or channel formed in the inner surface of the outer handle or ring 220. Any other suitable mechanisms and/or correspondingly shaped structures on the sleeve 222 that are configured to allow the sleeve 222 to connect to or operatively engage with the outer handle or ring 220 may also be used as would be recognized by one of skill in the art.

When the ring 220 is in a first or proximal position relative to the second handle 12 as shown in FIG. 31, the sleeve 222, which is operatively engaged with the outer handle or ring 220 as previously described, is also positioned at a proximal end 150 of the nut 142. The sleeve 222 holds the proximal end 150 of the nut 142 in a radially inwardly compressed condition and prevents such outward flaring of the nut 142. Thus, the sleeve 222 maintains and/or urges the nut 142 radially inwardly and urges the threads on the inner surface 152 of the nut 142 into engagement with the outer surface 122 of the main handle 10. Thus, when the ring 220 is in this first or proximal position on the second handle 12 (FIG. 31), the nut 142 is engaged with the main handle 10 such that the second handle 12 must be rotated to move the second handle 12 longitudinally in a distal direction.

However, during quick release, the ring 220 is moved from the first proximal position to a second distal position (see FIG. 33) by the user to move the sleeve 222 distally relative to the nut 142. As shown in FIG. 33, when the sleeve 222 is moved distally, the proximal end 150 of the nut 142 is permitted to expand radially outwardly or flare so that the inner surface 152 of the nut 142 is released from engagement with the main handle 10. In one example, the nut 142 is self-expanding, such that when the sleeve 222 is moved distally, the proximal end 150 of the nut 142 may expand radially outwardly without the aid or assistance of mechanical expansion techniques because the proximal end 150 of the nut 142 may have a tendency to flare radially outwardly in a natural or relaxed position. Shimstocks 151 may, if present, help facilitate such outward flaring to ensure that the nut 142 disengages from the main handle 10.

However, in another example, the nut 142 may also be mechanically expanded. In particular, as shown in FIG. 32, the proximal portion 228 of the sleeve 222 includes an expanding structure 230 that is configured to engage with at least a portion of the inner surface 152 of the nut 142 and urge the proximal end 150 of the nut 142 radially outwardly. Thus, as the sleeve 222 is moved distally, the expanding structure 230 comes into contact with the proximal end 150 of the nut 142 to radially outwardly expand the proximal end 150 of the nut 142. The inner surface 152 of the nut 142 thus becomes disengaged from the main handle 10 allowing the second handle 12 to be moved distally along the main handle 10 in a straight pull-back motion without rotation.

The expanding structure 230 may be in the form of a ring, partial ring, semi-circle, wedge and/or any other structure that facilitates radial expansion of the nut 142. As shown in FIGS. 31-33, the expanding structure 230 is a semi-circular structure that is located just proximal to and connected to the sleeve 222. The expanding structure 230 has a radius that is smaller than the radius of the sleeve 222. When the ring 220 is pulled distally back, the sleeve 222 with the expanding structure 230 also moves distally back. The expanding structure 230 drives itself between the outer surface 122 of the main handle 10 and the inner surface 152 of the proximal end 150 of the nut 142, thus urging the proximal end 150 of the nut 142 in a radially outwardly expanded condition. Thus, even if the nut 142 is self-expanding but somehow fails to self-expand upon movement of the ring 220 (and simultaneously, the sleeve 222) to a distal position, then the expanding structure 230 will facilitate the radially outward expansion of the proximal end 150 of the nut 142 to disengage the nut 142 from the main handle 10, allowing the quick release procedure to still be utilized. A self-expanding nut 142 may fail to sufficiently expand or become deformed so that it cannot fully disengage from the main handle 10 because of age and/or sterilization, for example. Alternatively, if the nut 142 is not self-expanding and is dependent on mechanical expansion, the expanding structure 230 serves to facilitate the radially outward expansion of the proximal end 150 of the nut 142 during the quick release procedure.

Figure 48:
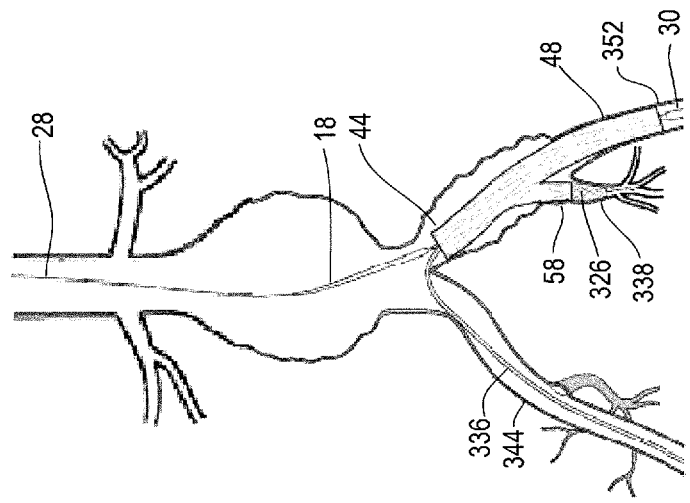
FIG. 48 illustrates the delivery device within a patient's vasculature with the sheath further retracted to expose the distal end of the stent graft.

The action of sliding outer ring 220 distally preferably also makes visible an arrow (or set of arrows or other similar markings) on the second handle 12 as shown in FIG. 21, which serve as an indicator to the user that the second handle 12 is ready for quick release by straight distal pull-back of the second handle relative to the main handle 10. At this time, with the proximal end 150 of the nut 142 flared radially outwardly as shown in FIG. 33, the second handle 12 is disengaged from the main handle 10 and can be slid distally towards the user in a straight pull-back motion (without rotation) so that further retraction of the sheath 104 to expose the distal end 48 of the stent graft 42 can be completed while simultaneously withdrawing the proximal and distal trigger wire(s) 84, 90, 208 to fully release the stent graft in the vasculature as shown in FIG. 48, thus accomplishing a quick release portion of the deployment procedure.

The operation of the delivery device 2, and in particular, one non-limiting example of a deployment sequence using the handle assembly 8 of the delivery device 2, will be described in reference to FIGS. 34-49. In this example, use of the delivery device 2 will be described in reference to the implantation of a stent graft 42 in one or more iliac arteries extending distally from the aorta 354 of a patient. After an incision is made in the femoral artery of the patient, the nose cone dilator 18 is inserted into the incision and the device 2 is tracked over a guide wire 28 and advanced through the ipsilateral external iliac artery 352 and common iliac artery 350 to the desired location for placement of the stent graft 42 at the site of an aneurysm 348 as shown in FIG. 34. The outer sheath 104 is disposed over the stent graft 42 and extends distally up to at least the distal end 82 of the nose cone dilator 18 during insertion and delivery to the target site, as shown in FIG. 34. As shown in detail in FIG. 35 and FIG. 36, the proximal end 184 of catheter 182 can be seen extending out of the proximal end of the sheath 104. A guide wire 190 extends through the lumen of the catheter 182.

Upon proper positioning at the target site using a desired imaging modality (i.e., by fluoroscopy, MRI, 3D or other imaging techniques) the guide wire 190 can be extended proximally through the pre-curved proximal end 184 of catheter 182, allowing it to be grasped by a snare 346 that has been extended proximally into the contralateral iliac artery 344. Once snared, the guide wire 190 can be pulled over the aortic bifurcation 342 and distally back down the contralateral iliac artery 344, as shown in FIGS. 37-39 to form a "through and through" guide wire 190.

Figure 39:
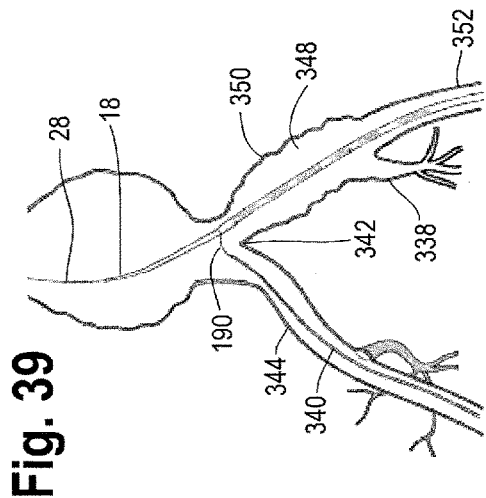
FIG. 39 illustrates an access sheath being tracked proximally over the guide wire.

As shown in FIG. 39, an access sheath 340 can be advanced over the through and through guide wire 190 until it is above the level of the aortic bifurcation 342 and/or abuts the proximal end 184 of the catheter 182. Using the desired imaging modality and one or more radiopaque markers (not shown) on the stent graft 42 and side arm 58, the user may ensure that the stent graft 42 is properly oriented such that the distal end of the side arm 58 is positioned above the origin of the internal iliac artery 338 to allow easy access into the internal iliac artery 338.

When the position of the device 2 is satisfactory, the user may partially withdraw sheath 104 as shown in FIG. 40. To withdraw the sheath 104, the user grasps the gripping portion 126 of the main handle 10 with one hand, and using the other hand, grasps the second handle 12. The second handle 12 may be rotated relative to the main handle 10 to move the second handle 12 distally along the main handle 10, thereby retracting the sheath 104 to expose at least a proximal portion of the stent graft 42. For example, the user may retract the sheath 104 to expose the proximal end 44 and continue to withdraw the sheath 104 until the distal end of the side arm 58 is exposed as shown in FIG. 41. At this stage, the user stops withdrawing the sheath 104 and the second handle 12 may be located at an intermediate position on the main handle 10, such as that shown in FIG. 21. It is noted that further sheath withdrawal at this stage may expose the distal end 48 of the stent graft 42 that extends into the external iliac artery 352, thus possibly limiting further positional changes of the stent graft 42. The access sheath 340 may be removed, such as by retracting it distally from the contralateral iliac artery 344, leaving the through and through wire 190 in place as shown in FIG. 41.

Figure 42:
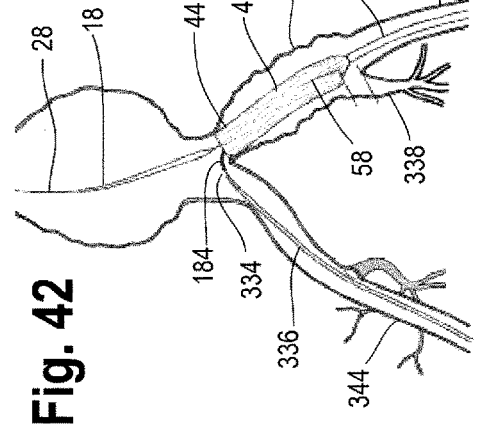
FIG. 42 illustrates an up and over sheath being tracked proximally through the contralateral iliac artery over the guide wire.

As shown in FIG. 42, an "up and over sheath" 336 can then be tracked proximally over the wire 190 through the contralateral iliac artery 344 until the proximal tip 334 of the up and over sheath 336 comes into contact with or abuts the pre-curved proximal end 184 of catheter 182. The user may continue to advance the up and over sheath 336 over the wire 190 so that the up and over sheath 336 advances over the aortic bifurcation 342 and into the proximal end 44 of the stent graft 42 and through the lumen of the side arm 58. Simultaneously, the catheter 182 is pushed distally by the tracking of the up and over sheath 336 over the wire 190. The up and over sheath 336 is tracked over the wire 190 until the proximal tip 334 of the up and over sheath 336 is adjacent to the distal end of the side arm 58 and/or extends distally out of the side arm 58 as shown in FIG. 43. The up and over sheath 336 can continue to be tracked over the wire 190 (while guide wire 190 extends distally into the proximal end 184 of the catheter 182 and through the lumen of the catheter 182 within the lumen of the sheath 104 as shown in an enlarged view in FIG. 45). At this stage, the user may wish to cannulate the ipsilateral internal iliac artery 338 as further described below.

In one non-limiting example of cannulating the internal iliac artery 338, the user may insert a secondary delivery assembly 332 through the lumen of the up and over sheath 336 as shown in FIGS. 44 and 45. The secondary delivery assembly 332 may comprise a delivery catheter 330 having a guide wire 328 extending there through. As FIGS. 44 and 45 show, the secondary delivery assembly 332 comprising the delivery catheter 330 and guide wire 328 is further advanced through the up and over sheath 336 and into the opening of the internal iliac artery 338. With the delivery catheter 330 extending into the opening of the internal iliac artery 338, the guide wire 328 may be replaced with a stiffer wire, such as a Rosen or AES wire guide, if desired.

Next, as shown in FIGS. 46 and 47, the delivery catheter 330 may be removed from the up and over sheath 336, leaving the up and over sheath 336 and guide wire 328 in place. At this time, as shown in FIG. 47, a secondary stent graft 326 can be tracked over the guide wire 328 and extended into the internal iliac artery 338. The secondary stent graft 326 may, in one non-limiting example, comprise a self-expanding stent graft and/or a balloon-expandable stent graft sized and configured for delivery and deployment in the internal iliac artery 338. The secondary stent graft 326 may be delivered to the internal iliac artery 338 in a number of acceptable ways as would be understood by one of skill in the art, including but not limited to the secondary stent graft 326 being pre-loaded onto an auxiliary delivery device (not shown) and/or retained in a delivery configuration within a secondary sheath (not shown) to facilitate introduction and delivery of the secondary stent graft 326 over the guide wire 328 (and within the up and over sheath 336) to a desired location within the vasculature. A suitable combination of the secondary stent graft 326 and an auxiliary delivery device (not shown) or a secondary sheath (not shown) may be selected such that the auxiliary delivery device (not shown) or a secondary sheath (not shown) can pass through the up and over sheath 336 in a co-axial manner while allowing the through and through guide wire 190 to remain in place. The secondary stent graft 326 extends distally from the distal end of side arm 58, thus serving as an extension of the side arm 58 and maintaining and/or restoring patency to the internal iliac artery 338.

At this stage, the sheath 104 may be retracted further distally to expose the distal end 48 of the stent graft 42 as shown in FIG. 48. Further retraction of sheath 104 may be accomplished by again moving second handle 12 back in a distal direction relative to the main handle 10 by the user to a position as shown in FIGS. 23 and 24 while simultaneously withdrawing the proximal trigger wires 84, 90 and the distal trigger wires 208 to thereby deploy the stent graft 42 as shown in FIG. 48.

To accomplish this proximal and distal trigger wire removal and deployment of the distal end 48 of the stent graft 42, the user may continue rotation of the second handle 12 or, alternatively, the user may employ the quick release procedure as described above, which permits longitudinal movement of the second handle 12 relative to the main handle 10 without having to rotate the second handle 12. Whether by continued rotation of the second handle 12 relative to the main handle 10 or by implementation of the quick release procedure (allowing straight pull-back of the second handle without rotation), the user moves the second handle 12 distally along the main handle 10 for a travel distance indicated generally by reference number 212 in FIG. 21. In one non-limiting example, this travel distance 212 may be the distance of longitudinal movement of the second handle 12 necessary to facilitate distal retraction of the sheath 104 a sufficient distance to expose the distal end 48 or the stent graft, such that the stent graft 42 is completely un-sheathed. By this same action, the proximal and distal trigger wire or wires 84, 90, 208 are also withdrawn from the stent graft 42 to complete the stent graft deployment. In the event of a mechanical malfunction of one or more components of the handle assembly 8 described above, the handle end cap 14 can be removed, and the interior 124 of the main handle 10 can be accessed and manipulated manually to perform certain deployment steps such as allowing the user to manually pull back on the trigger wire release mechanism 204 to release the trigger wires from the stent graft.

Once the stent graft 42 has been fully released from the delivery device 2 as shown in FIG. 48, the up and over sheath 336 can be withdrawn distally to a suitable position to allow deployment of the secondary stent graft 326. As previously mentioned, the secondary stent graft 326 may have self-expanding properties and/or it may be expanded by mechanical means, such as by balloon expansion.

Figure 49:
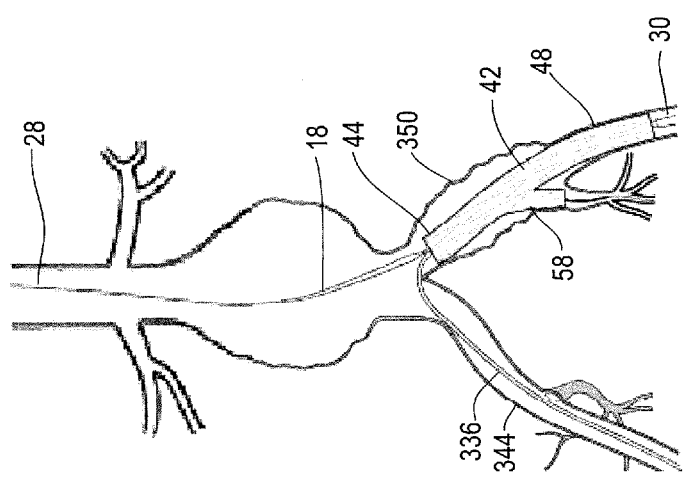
FIG. 49 illustrates the stent graft and secondary stent graft deployed within the patient's vasculature.
Figure 50:
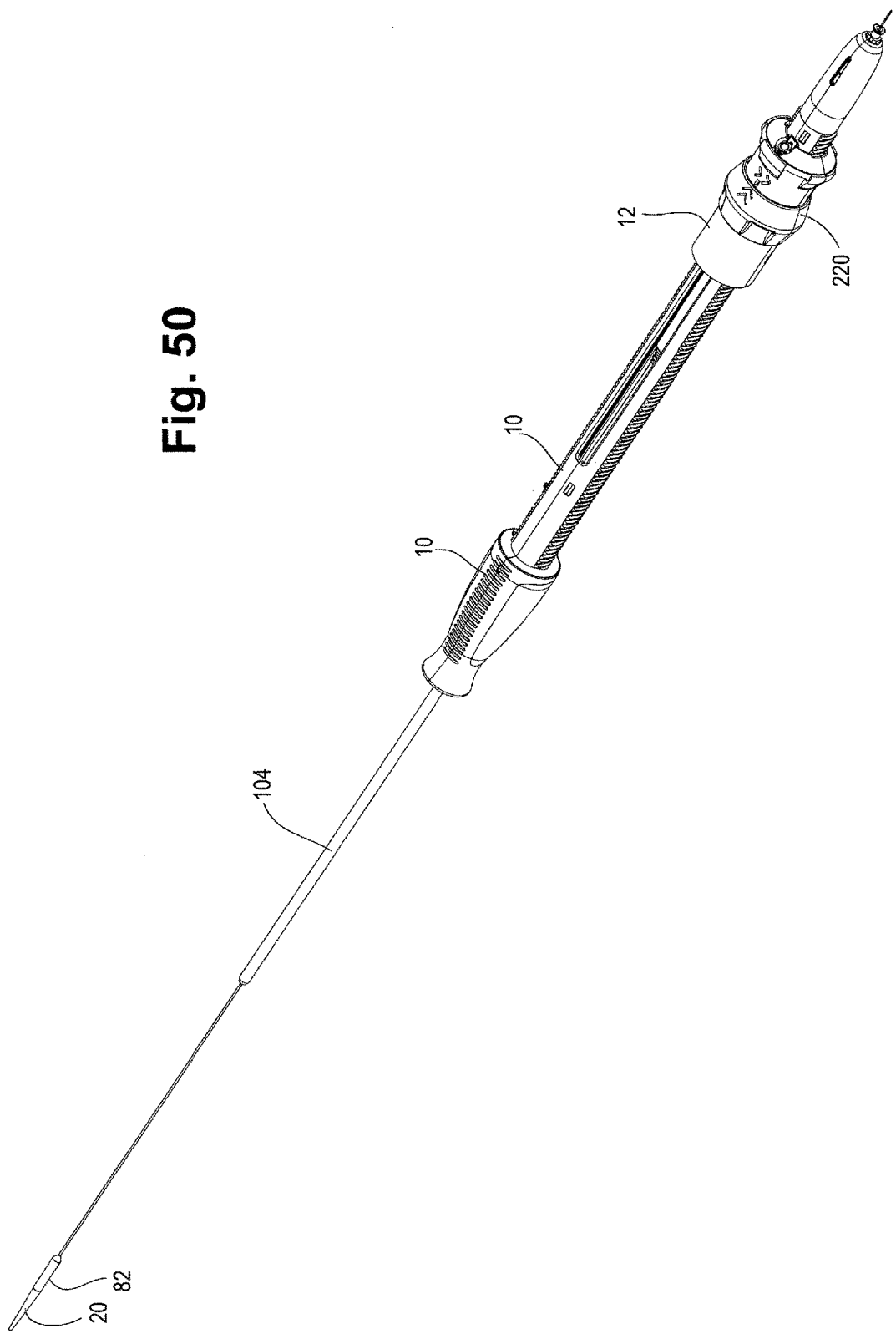
FIG. 50 is a perspective view of the delivery device with the sheath fully retracted and the stent graft deployed therefrom.

Following deployment, and with the stent graft 42 released from the stent graft retention region 16 of the delivery device 2 as shown in FIG. 50 and the secondary stent graft 326 expanded within the vasculature as shown in FIG. 49, it may be desirable to withdraw the delivery device 2 from the patient's body. In some instances, such as if delivery and deployment of an AAA main body stent graft for deployment in the aorta 354 is desired, the guide wire 28 may be left in place even after the delivery device 2 is removed from the vasculature to facilitate tracking of another delivery device (not shown) for the delivery and deployment of an AAA main body stent graft.

When removing the delivery device 2 from the patient, if the quick release procedure described above has already been employed, then the nut 142 has already been disengaged or disassociated from the main handle 10, allowing the second handle 12 to slide freely longitudinally along the main handle 10. Thus, the user can slide the second handle 12 in a proximal direction (away from the user) on the main handle 10, thus sliding the sheath connector 108 and sheath 104 proximally and allowing the proximal end of the sheath 104 to extend over all of, part of, or at least distal portion 82 of the nose cone dilator 18 of the device 2 so as to "hub" or "recapture" a portion of the nose cone within the sheath 104 as shown in FIG. 51.

Alternatively, rather than pushing the second handle 12 proximately to re-sheath the nose cone dilator 18, the main handle 10 may be pulled distally relative to the second handle 12, thus pulling the distal portion 82 of the nose cone dilator 18 into the proximal end of the sheath 104. With at least a distal portion 82 of the nose cone dilator 18 recaptured within the sheath 104, the delivery device 2 can be withdrawn from the patient's body.

If, however, the user did not employ the quick release procedure for trigger wire release (but instead the user decided to continue rotating the second handle 12 to move it distally relative to the main handle 10 to accomplish these deployment steps), then, at this time, the second handle 12 is at a distal most position on the main handle (see FIGS. 23 and 24) but the inner surface of the nut 142 is still threadedly engaged with the outer surface 122 of the main handle 10. Thus, in order to move the sheath 104 proximally for tip re-sheathing or recapture, the user must first move the ring 220 distally on the second handle 12 to move the sleeve 222 distally, allowing the proximal end 150 of the nut 142 to flare or expand radially outwardly and disengage from the threads 132 on the main handle 10. This permits the second handle 12 to now slide freely longitudinally on the main handle 10 and the user may then be able to move the second handle 12 proximally to recapture (re-sheath) at least a distal portion 82 of the nose cone dilator 18 as previously described and shown in FIG. 51, and then remove the delivery device 2 from the patient to complete the procedure, thus having effectively and efficiently deployed a stent graft 42 (and secondary stent graft 326) into one or more branched vessels, including, but not limited to a common iliac artery and the external and internal iliac arteries extending therefrom, in order to treat and/or restore patency to one or both of such vessels.

Throughout this specification, unless the context requires otherwise, the words "comprise" and "include" and variations such as "comprising" and "including" will be understood to imply the inclusion of an item or group of items, but not the exclusion of any other item or group items. While various examples of the invention have been described, it will be apparent to those of ordinary skill in the art that many more examples and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. A handle assembly for a prosthesis delivery device comprising:
    a stationary main handle comprising a proximal end and a distal end and sidewall extending there between to define a main handle housing interior;
    a second handle disposed at least partially on the main handle and longitudinally moveable relative to the stationary main handle;
    a trigger wire release mechanism disposed in the main handle housing interior;
    wherein at least one proximal trigger wire extends from the trigger wire release mechanism to a proximal end of a prosthesis and wherein at least one distal trigger wire extends from the trigger wire release mechanism to a distal end of the prosthesis;
    wherein longitudinal movement of the second handle relative to the stationary main handle causes retraction of the trigger wire release mechanism within the main handle housing interior, thereby releasing the at least one proximal trigger wire from the proximal end of the prosthesis and releasing the at least one distal trigger wire from the distal end of the prosthesis.

2. The handle assembly of claim 1, wherein rotation of the second handle imparts longitudinal movement of the second handle relative to the main handle.

3. The handle assembly of claim 1 wherein the second handle has a first position on the main handle in which release of the at least one proximal trigger wire and the at least one distal trigger wire is prevented and a second position on the main handle in which release of the at least one proximal trigger wire and the at least one distal trigger wire is permitted.

4. The handle assembly of claim 1 wherein at least two proximal trigger wires extend from the trigger wire release mechanism to the proximal end of the prosthesis.

5. The handle assembly of claim 1, further comprising a sheath operatively connected to the second handle, the sheath extending proximally of the main handle, wherein the at least one of circumferential and longitudinal movement of the second handle relative to the main handle retracts the sheath in a distal direction.

6. The handle assembly of claim 5 wherein retraction of the sheath in a distal direction exposes at least a proximal end of the prosthesis.

7. The handle assembly of claim 6 wherein the at least one proximal trigger wire and the at least one distal trigger wire cannot be released from the prosthesis until the sheath has been retracted to expose at least the proximal end of the prosthesis.

8. The handle assembly of claim 5, wherein upon longitudinal movement of the second handle relative to the main handle from a first position to a second position, the sheath is distally retracted to expose at least a proximal end of the prosthesis and wherein upon movement of the second handle relative to the main handle from the second position to a third position, the trigger wire release mechanism moves longitudinally within the main handle housing interior to release the at least one proximal trigger wire from the proximal end of the prosthesis and release the at least one distal trigger wire from the distal end of the prosthesis.

9. The handle assembly of claim 1, wherein the trigger wire release mechanism comprises a ring that is longitudinally slideable within the main handle housing interior, and wherein a distal end of the at least one proximal trigger wire and a distal end of the at least one distal trigger wire are attached to the ring.

10. The handle assembly of claim 9 further comprising a resilient member extending longitudinally within the main handle housing interior, the resilient member having a proximal end and a distal end and defining a tubular passageway there between, wherein the at least one proximal trigger wire and the at least one distal trigger wire extend proximally from the trigger wire release mechanism through the tubular passageway of the resilient member.

11. The handle assembly of claim 10 wherein when the second handle is in a first position relative to the main handle, the resilient member is in an expanded condition and wherein when the second handle is in a second position relative to the main handle, the resilient member is in a contracted condition.

12. The handle assembly of claim 1, further comprising a catheter hub positioned within the main handle housing interior.

13. The handle assembly of claim 12 wherein a catheter extends at least partially through the catheter hub and extends proximally through the main handle housing interior and extends further proximally through a lumen of the prosthesis.

14. The handle assembly of claim 1, wherein an inner surface of the second handle comprises internal threads that are engageable with external threads on the sidewall of the main handle.

15. A delivery system for delivering a prosthesis, the delivery system comprising:
  a proximal end and a distal end;
  a prosthesis retention region at the proximal end of the delivery system;
  a prosthesis having a proximal end and a distal end and a sidewall extending there between, and a side arm extending from the sidewall of the prosthesis between the proximal and distal ends, wherein the prosthesis is releasably coupled to the prosthesis retention region of the delivery system;
  a handle assembly disposed at the distal end of the delivery system, wherein the handle assembly comprises:
    a stationary main handle comprising a proximal end and a distal end and sidewall extending there between to define a main handle housing interior;
    a second handle disposed at least partially on the stationary main handle and longitudinally moveable relative to the stationary main handle;
    a trigger wire release mechanism disposed in the main handle housing interior, the trigger wire release mechanism having a first position within the main handle housing in which the prosthesis is retained in a delivery configuration and a second position in which the prosthesis is in a deployed configuration;
    a sheath operatively connected to the second handle and extending proximally of the stationary main handle, the sheath having a first position wherein the prosthesis is covered by the sheath and a second position, and wherein longitudinal movement of the second handle relative to the stationary main handle retracts the sheath in a distal direction from the first position to the second position; and
    wherein movement of the trigger wire release mechanism from the first position to the second deployed position is prevented when the sheath is in the first position.

16. The delivery system of claim 15 wherein when the trigger wire release mechanism is in the first position, at least one proximal trigger wire extends from the trigger wire release mechanism to the proximal end of the prosthesis and wherein at least one distal trigger wire extends from the trigger wire release mechanism to the distal end of the prosthesis to radially inwardly retain the prosthesis in a delivery configuration.

17. The delivery system of claim 15 wherein the second handle has a first position relative to the main handle in which the prosthesis is covered by the sheath, a second position in which at least the proximal end of the prosthesis is exposed and a third position in which the prosthesis is fully exposed.

18. The delivery system of claim 17 wherein movement of the second handle from the first position to the second position retracts the sheath to expose at least the proximal end of the prosthesis and wherein movement of the second handle from the second position to the third position fully exposes the prosthesis and simultaneously retracts the trigger wire release mechanism within the main handle housing interior from the first position to the second position, thereby releasing the at least one proximal trigger wire from the proximal end of the prosthesis and releasing the at least one distal trigger wire from the distal end of the prosthesis.

19. The delivery system of claim 15 further comprising a catheter extending proximally from the main handle housing interior to the stent graft retention region, the catheter further extending through a lumen of the side arm and proximally to the proximal end of the prosthesis.

20. The delivery system of claim 19 further comprising a nose cone extending proximally from the prosthesis retention region, the nose cone comprising a groove formed in an outer surface thereof and wherein a proximal end of the catheter extends within at least a portion of the groove.

* * * * *